US010603079B2

(12) United States Patent
Rice et al.

(10) Patent No.: US 10,603,079 B2
(45) Date of Patent: Mar. 31, 2020

(54) SYSTEM AND METHOD FOR INSERTION OF FLEXIBLE SPINAL STABILIZATION ELEMENT

(71) Applicant: Zimmer Spine, Inc., Edina, MN (US)

(72) Inventors: Mark W Darst Rice, Minneapolis, MN (US); Emmanuel Zylber, Marseilles (FR)

(73) Assignee: Zimmer Spine, Inc., Edina, MN (US)

( * ) Notice: Subject to any disclaimer, the term of this patent is extended or adjusted under 35 U.S.C. 154(b) by 0 days.

(21) Appl. No.: 15/718,052

(22) Filed: Sep. 28, 2017

(65) Prior Publication Data

US 2018/0014856 A1    Jan. 18, 2018

Related U.S. Application Data

(63) Continuation of application No. 14/800,309, filed on Jul. 15, 2015, now Pat. No. 9,782,203, which is a
(Continued)

(51) Int. Cl.
*A61B 17/70* (2006.01)
*A61B 17/88* (2006.01)
*A61B 90/00* (2016.01)

(52) U.S. Cl.
CPC ...... *A61B 17/7031* (2013.01); *A61B 17/7022* (2013.01); *A61B 17/7032* (2013.01);
(Continued)

(58) Field of Classification Search
CPC . A61B 17/701; A61B 17/7019; A61B 17/702; A61B 17/7022; A61B 17/7026;
(Continued)

(56) References Cited

U.S. PATENT DOCUMENTS 5,318,566 A * 6/1994 Miller ................. A61B 17/823
606/60
5,562,660 A 10/1996 Grob
(Continued)

FOREIGN PATENT DOCUMENTS

CN    102014776 A    4/2011
EP      2047815 A1    4/2009
(Continued)

OTHER PUBLICATIONS

"U.S. Appl. No. 12/025,984, Advisory Action dated Sep. 4, 2014", 3 pgs.
(Continued)

*Primary Examiner* — Lynnsy M Summitt
(74) *Attorney, Agent, or Firm* — Schwegman Lundberg & Woessner, P.A.

(57) ABSTRACT

A method of inserting a spinal stabilization system into a patient generally comprises inserting a first positioning tool through a first location on a patient's skin and along a path generally toward a first vertebral anchor, coupling an end of the first positioning tool to the first vertebral anchor, positioning at least a portion of a delivery device over a connecting element, and inserting the delivery device and the connecting element through the patient's skin at the first location and along at least a portion of the first positioning tool. The first positioning tool is configured to facilitate directing the delivery device and connecting element generally toward a second vertebral anchor within the patient's body.

19 Claims, 17 Drawing Sheets

Related U.S. Application Data continuation of application No. 12/025,984, filed on Feb. 5, 2008, now Pat. No. 9,277,940.

(52) U.S. Cl.
CPC ...... *A61B 17/7085* (2013.01); *A61B 17/8869* (2013.01); *A61B 17/7004* (2013.01); *A61B 17/7008* (2013.01); *A61B 2090/3983* (2016.02)

(58) Field of Classification Search
CPC ............ A61B 17/7029; A61B 17/7031; A61B 17/7083; A61B 17/82; A61B 17/842; A61B 17/8869; A61B 17/7014; A61B 17/7041; A61B 17/7043; A61B 17/7044; A61B 17/7053

See application file for complete search history.

(56) References Cited

U.S. PATENT DOCUMENTS

| | | | |
|---|---|---|---|
| 6,290,700 B1 | 9/2001 | Schmotzer | |
| 6,616,667 B1* | 9/2003 | Steiger | A61B 17/8861 606/103 |
| 6,648,888 B1 | 11/2003 | Shluzas | |
| 6,821,277 B2* | 11/2004 | Teitelbaum | A61B 17/1671 606/262 |
| 7,073,415 B2* | 7/2006 | Casutt | A61B 17/7008 606/104 |
| 7,094,240 B2* | 8/2006 | Molz, IV | A61B 17/88 606/103 |
| 7,275,336 B2* | 10/2007 | Casutt | A61B 90/06 33/512 |
| 7,708,763 B2 | 5/2010 | Selover et al. | |
| 7,922,725 B2* | 4/2011 | Darst Rice | A61B 17/8869 606/254 |
| 8,043,343 B2* | 10/2011 | Miller | A61B 17/7037 606/246 |
| 8,216,245 B2* | 7/2012 | Gil | A61B 17/7022 606/103 |
| 8,226,656 B2* | 7/2012 | McBride | A61B 17/7004 606/250 |
| 8,267,968 B2* | 9/2012 | Remington | A61B 17/7085 606/264 |
| 8,328,849 B2* | 12/2012 | Nydegger | A61B 17/7022 606/254 |
| 8,465,495 B2* | 6/2013 | Belliard | A61B 17/8869 606/103 |
| 8,540,720 B2* | 9/2013 | Garcia-Bengochea | A61B 17/7085 606/86 A |
| 9,277,940 B2 | 3/2016 | Rice | |
| 9,339,303 B2* | 5/2016 | Calvosa | A61B 17/7007 |
| 9,339,309 B1* | 5/2016 | Geist | A61B 17/7083 |
| 9,526,525 B2* | 12/2016 | Remington | A61B 17/7005 |
| 9,757,167 B2* | 9/2017 | Hsu | A61B 17/7076 |
| 9,782,203 B2 | 10/2017 | Rice | |
| 10,022,172 B2* | 7/2018 | Boyd | A61B 17/1757 |
| 2002/0035366 A1 | 3/2002 | Walder et al. | |
| 2003/0060826 A1 | 3/2003 | Foley et al. | |
| 2004/0087950 A1 | 5/2004 | Teitelbaum | |
| 2004/0143264 A1 | 7/2004 | Mcafee | |
| 2005/0010220 A1 | 1/2005 | Casutt et al. | |
| 2005/0131407 A1* | 6/2005 | Sicvol | A61B 17/7004 606/262 |
| 2005/0192589 A1 | 9/2005 | Raymond et al. | |
| 2005/0277922 A1 | 12/2005 | Trieu et al. | |
| 2006/0036255 A1 | 2/2006 | Pond, Jr. et al. | |
| 2006/0074418 A1 | 4/2006 | Jackson | |
| 2006/0111715 A1 | 5/2006 | Jackson | |
| 2006/0149238 A1 | 7/2006 | Sherman et al. | |
| 2006/0149242 A1 | 7/2006 | Kraus et al. | |
| 2006/0195090 A1 | 8/2006 | Suddaby | |
| 2006/0247630 A1 | 11/2006 | Iott et al. | |
| 2007/0005063 A1 | 1/2007 | Bruneau et al. | |
| 2007/0042633 A1 | 2/2007 | Frigg | |
| 2007/0078460 A1 | 4/2007 | Frigg et al. | |
| 2007/0083210 A1* | 4/2007 | Hestad | A61B 17/17 606/86 R |
| 2007/0118119 A1* | 5/2007 | Hestad | A61B 17/3421 606/86 A |
| 2007/0191836 A1 | 8/2007 | Justis | |
| 2007/0233075 A1 | 10/2007 | Dawson | |
| 2007/0270860 A1 | 11/2007 | Jackson | |
| 2007/0288011 A1 | 12/2007 | Logan | |
| 2007/0299443 A1 | 12/2007 | Dipoto et al. | |
| 2008/0009863 A1* | 1/2008 | Bond | A61B 17/025 606/86 A |
| 2008/0015582 A1* | 1/2008 | DiPoto | A61B 17/02 606/86 A |
| 2008/0021459 A1 | 1/2008 | Lim | |
| 2008/0051787 A1* | 2/2008 | Remington | A61B 17/7005 606/279 |
| 2008/0140133 A1 | 6/2008 | Allard et al. | |
| 2008/0177317 A1 | 7/2008 | Jackson | |
| 2008/0234738 A1 | 9/2008 | Zylber et al. | |
| 2008/0249531 A1 | 10/2008 | Patterson | |
| 2008/0275456 A1 | 11/2008 | Vonwiller et al. | |
| 2008/0294198 A1 | 11/2008 | Jackson | |
| 2008/0312704 A1* | 12/2008 | Hestad | A61B 17/7085 606/86 A |
| 2009/0088799 A1* | 4/2009 | Yeh | A61B 17/7005 606/246 |
| 2009/0198281 A1 | 8/2009 | Rice et al. | |
| 2009/0204118 A1* | 8/2009 | Pratt | A61B 17/82 606/74 |
| 2015/0313644 A1 | 11/2015 | Rice et al. | |

FOREIGN PATENT DOCUMENTS

| | | |
|---|---|---|
| EP | 2254494 | 6/2012 |
| WO | WO-2009099477 | 8/2009 |

OTHER PUBLICATIONS

"U.S. Appl. No. 12/025,984, Advisory Action dated Oct. 19, 2011", 4 pgs.

"U.S. Appl. No. 12/025,984, Final Office Action dated Aug. 11, 2011", 27 pgs.

"U.S. Appl. No. 12/025,984, Non Final Office Action dated Jan. 15, 2014", 21 pgs.

"U.S. Appl. No. 12/025,984, Non Final Office Action dated Mar. 21, 2011", 34 pgs.

"U.S. Appl. No. 12/025,984, Non Final Office Action dated Jun. 30, 2014", 31 pgs.

"U.S. Appl. No. 12/025,984, Notice of Allowance dated Nov. 3, 2015", 13 pgs.

"U.S. Appl. No. 14/800,309, Final Office Action dated Mar. 24, 2017", 12 pgs.

"U.S. Appl. No. 14/800,309, Non Final Office Action dated Oct. 20, 2016", 8 pgs.

"U.S. Appl. No. 14/800,309, Notice of Allowance dated Jun. 5, 2017", 9 pgs.

"U.S. Appl. No. 14/800,309, Preliminary Amendment filed Jan. 7, 2016", 5 pgs.

"U.S. Appl. No. 14/800,309, Response filed Feb. 16, 2017 to Non Final Office Action dated Oct. 20, 2016", 9 pgs.

"U.S. Appl. No. 14/800,309, Response filed May 18, 2017 to Final Office Action dated Mar. 24, 2017", 10 pgs.

"European Application Serial No. 08872028.9, Communication Pursuant to Article 94(3) EPC dated Mar. 15, 2011", 5 pgs.

"European Application Serial No. 08872028.9, Communication pursuant to Rules 161(2) and 162 EPC dated Sep. 27, 2010", 2 pgs.

"European Application Serial No. 08872028.9, Decision to grant dated May 24, 2012", 2 pgs.

"European Application Serial No. 08872028.9, Office Action dated Dec. 29, 2011", 4 pgs.

(56) References Cited

OTHER PUBLICATIONS

"European Application Serial No. 08872028.9, Response filed Jul. 20, 2011 to Communication Pursuant to Article 94(3) EPC dated Mar. 15, 2011", 15 pgs.

"International Application Serial No. PCT/US2008/085002, International Preliminary Report on Patentability dated Aug. 10, 2010", 7 pgs.

"International Application Serial No. PCT/US2008/085002, International Search Report dated Nov. 19, 2009", 4 pgs.

"International Application Serial No. PCT/US2008/085002, Written Opinion dated Nov. 19, 2009", 6 pgs.

"U.S. Appl. No. 15/718,052, Response filed Sep. 16, 2019 to Final Office Action dated Jun. 14, 2019", 8 pages.

* cited by examiner

SYSTEM AND METHOD FOR INSERTION OF FLEXIBLE SPINAL STABILIZATION ELEMENT

CROSS-REFERENCE RELATED APPLICATIONS

This application is a continuation of U.S. patent application Ser. No. 14/800,309, filed Jul. 15, 2015, which will issue on Oct. 10, 2017 as U.S. Pat. No. 9,782,203, which application is a continuation of U.S. patent application Ser. No. 12/025,984, filed Feb. 5, 2008, which issued on Mar. 8, 2016 as U.S. Pat. No. 9,277,940, the contents of which are fully incorporated herein by reference in their entireties.

FIELD OF THE INVENTION

This invention relates to surgical methods and associated installation systems for spinal stabilization, and more particularly to such methods and systems that facilitate inserting a flexible spinal stabilization element into a patient.

BACKGROUND

One of the most common methods for treating abnormal curvature of the spine and spinal disorders is to immobilize a portion of the spine to allow treatment. Traditionally, immobilization has been accomplished by rigid stabilization. For example, in a conventional spinal fusion procedure, a rigid fixation rod is installed between pedicle screws secured to adjacent vertebrae. The fixation rod cooperates with the screws to immobilize the two vertebrae relative to each other so that fusion may occur.

More recently, dynamic stabilization has been used in spinal treatment procedures. Dynamic stabilization permits enhanced mobility of the spine while also providing sufficient stabilization to effect treatment. One example of a dynamic stabilization system is the Dynesys® system available from Zimmer Spine, Inc. of Edina, Minn. Such dynamic stabilization systems typically include a flexible, tubular spacer positioned between pedicle screws installed in adjacent vertebrae of the spine. The spacer is positioned between the pedicle screws and a flexible cord is threaded through the spacer. The flexible cord is also secured to heads of the pedicle screws by set screws, thereby retaining the spacer between the pedicle screws while cooperating with the spacer to permit mobility of the spine.

The dynamic stabilization systems described above and others are installed in a patient during a surgical procedure. Patient recovery from such surgical procedures is greatly enhanced if the tissue, muscle, and other parts of the patient that are displaced and affected by the surgery are minimized, including the size and severity of the required incisions. For example, the cord may be inserted through an incision used to implant one of the pedicle screws and then advanced to its installed position between the pedicle screws. Due to its flexible nature, however, the cord can be difficult to maneuver through the tissue. Therefore, systems and methods that facilitate the insertion of such flexible cords and similar elements are highly desirable.

SUMMARY

A method of inserting a spinal stabilization system into a patient generally comprises inserting a first positioning tool through a first location on a patient's skin and along a path generally toward a first vertebral anchor within the patient's body. An end of the first positioning tool is then coupled to the first vertebral anchor. After positioning at least a portion of a delivery device over a connecting element, the delivery device and the connecting element are inserted through the patient's skin at the first location and along at least a portion of the first positioning tool. The first positioning tool is configured to facilitate insertion of the delivery device and connecting element, the delivery device and connecting element being directing generally toward a second vertebral anchor within the patient's body. Eventually, a first portion of the connecting element is secured to the second vertebral anchor and the delivery device is removed from the connecting element to expose a second portion of the connecting element. A spacer may then be advanced over the connecting element before securing the second portion to the first vertebral anchor.

In one embodiment, at least a portion of the delivery device is received in an elongated slot defined by the first positioning tool when inserted through the patient's skin. After securing the first portion of the connecting element to the second vertebral anchor and removing the delivery device to expose the second portion of the connecting element, the second portion is positioned within the elongated slot. A tensioning tool may be inserted through the elongated slot to direct the second portion into a receiving channel defined by the first vertebral anchor. Additional length of the connecting element extending beyond of the receiving channel may be pulled to place the connecting element in tension before securing the second portion to the first vertebral anchor.

In another embodiment, the spinal stabilization system further includes a third vertebral anchor positioned between the first and second vertebral anchors. Using the techniques briefly described above and set forth in greater detail below, the connecting element is secured to the first, second, and third vertebral anchors so as to form a multi-level treatment system.

In another aspect or embodiment, at least two spacers for can be provided for placement between the vertebral anchors, the first spacer having a first elasticity and placed between first and second vertebral anchors and the second spacer having a second elasticity placed between second and third vertebral anchors.

In another embodiment, the connecting element for connection to the vertebral anchors can include a first portion with a first elasticity for connection between the first and second vertebral anchors and a second portion with a second elasticity for connection between the second and third vertebral anchors.

A system for dynamic stabilization system of a patient's spine is also provided. The system generally comprises first and second vertebral anchors configured to be secured at first and second locations within the patient's body, a connecting element having first and second portions configured to be received by the first and second vertebral anchors a delivery device configured to be positioned over the connecting element, and a first positioning tool having an end configured to couple to the first vertebral anchor. The delivery device is more rigid than the connecting element and is retractable along the connecting element. Additionally, the first positioning tool includes an elongated slot configured to facilitate guiding the delivery device and connecting element along a path generally toward the second vertebral anchor.

In one aspect or embodiment, the delivery device includes a first sheath member coupled to a second sheath member at an articulating joint so that the angle of the first sheath member relative to the second sheath member may be adjusted. The articulating joint may be configured to lock the first sheath member at various angles relative to the second sheath member.

In another aspect or embodiment, a plurality of spacers having different elastic characteristics may be provided, allowing the surgeon to select a spacer based on its rigidity or elasticity to treat specific patient conditions. A plurality of connecting elements having different elastic characteristics may also be provided, allowing the surgeon to select a connecting element based on its rigidity or elasticity to treat specific patient conditions.

BRIEF DESCRIPTION OF THE DRAWINGS

The accompanying drawings, which are incorporated in and constitute a part of this specification, illustrate exemplary embodiments of the invention.

DETAILED DESCRIPTION

Figure 1:
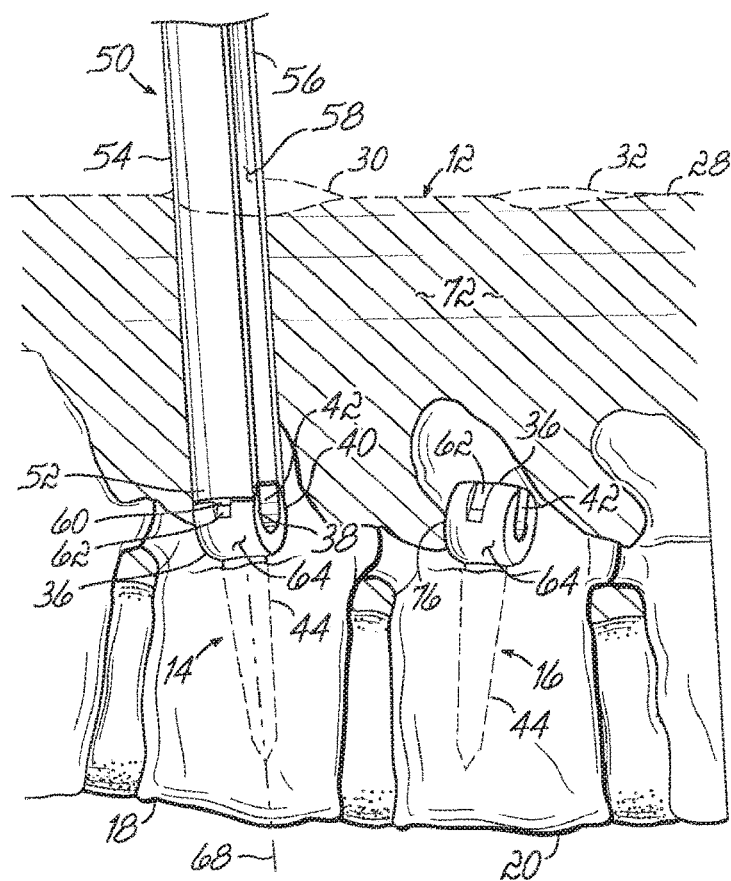
FIG. 1 is a schematic view showing a portion of a spinal stabilization system according to one embodiment.
Figure 1A:
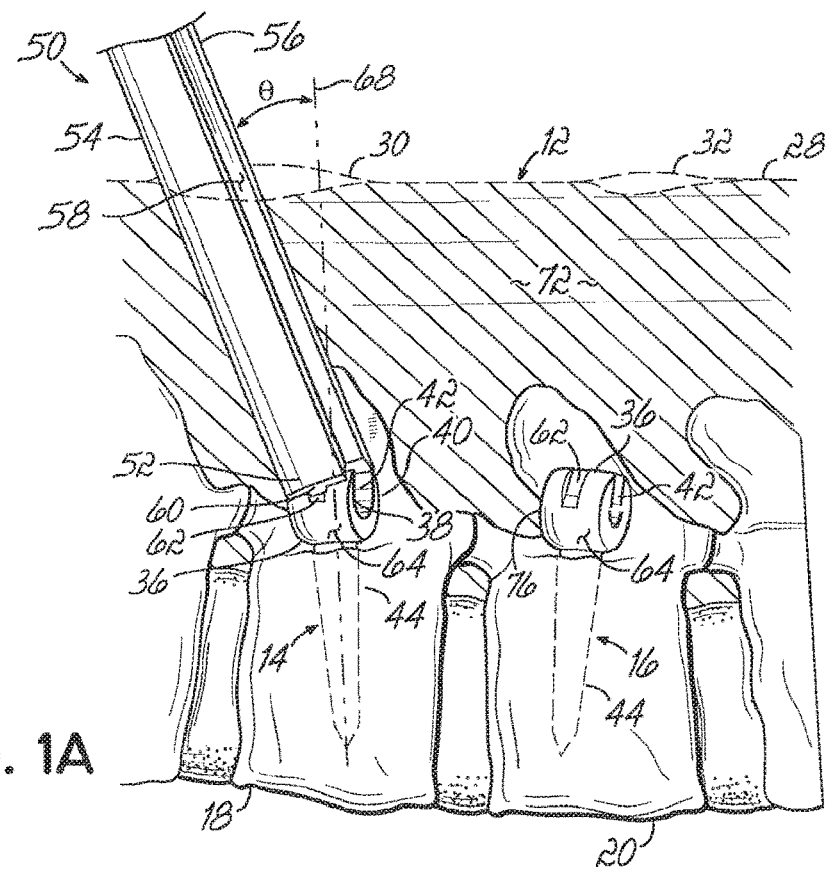
FIG. 1A is a schematic view showing a positioning tool in the spinal stabilization system of FIG. 1.

The following description focuses primarily upon techniques and tools for inserting the components of a stabilization system 10 (FIG. 3G) within a patient's body 12. However, by way of background and with reference to FIG. 3G, the stabilization system 10 generally includes first and second vertebral anchors 14, 16 secured to respective first and second vertebrae 18, 20 in the patient's body 12, a connecting element 22 configured to extend between the first and second anchors 14, 16, and a spacer, configured to be received over the connecting element 22 between the first and second vertebral anchors 18, 20. The connecting element 22 may be, for example and without limitation, a flexible element such as a cord formed from polyethylene terephthalate (PET), titanium or metal materials, or other suitable materials recognized by those skilled in the art. In one embodiment, the surgeon can be provided with several connecting elements 22 of varying elasticity to allow the surgeon to choose the connecting element based on the patient's condition.

The spacer 24 may be a flexible element formed, for example and without limitation, from polycarbonate-urethane (PCU), PEEK, polymeric and/or flexible materials, or other suitable materials recognized by those skilled in the art. In alternative embodiments, the spacer can be formed from a rigid material. In one embodiment, the stabilization system 10 includes elements of the Dynesys® system available from Zimmer Spine, Inc. of Edina, Minn. Those skilled in the art will appreciate, however, that the techniques and tools described below may also apply to other stabilization systems having similar components and/or operating upon similar principles.

Additionally, those skilled in the art will appreciate that the stabilization system can be used in connection with other spinal implants, such as interbody fusion implants, biologic materials, artificial disks, nucleus repair materials, nucleus replacement implants, plates, screws, vertebral body replacement implants, interspinous process spacer implants, bone void filler materials and bone cement materials.

The first and second vertebral anchors 14, 16 may be inserted into the patient's body 12 and secured using any technique known in the art. In one embodiment, a first incision 30 is made at a first location on the patient's skin 28 generally aligned above the first vertebra 18. The first vertebral anchor 14 is inserted through the first incision 30 and advanced through the patient's body 12 so that it may be secured to the first vertebra 18.

The second vertebral anchor 16 may be inserted into the patient's body 12 in a similar manner. Specifically, a second incision 32 may be made at a second location on the patient's skin 28 generally aligned above the second vertebra 20. The second vertebral anchor 16 is advanced into the patient's body 12 so that it may be secured to the second vertebra 20. Advantageously, the first and second incisions 30, 32 may be sized so that minimally invasive, percutaneous techniques and/or retractor-based techniques may be used to advance and install the first and second vertebral anchors 14, 16 in the patient's body 12. However, the first and second incisions 30, 32 may alternatively be sized for traditional, open surgical procedures as well.

A wide variety of vertebral anchors may be used with the stabilization system 10. The first and second vertebral anchors 14, 16 shown in the drawings are uniaxial pedicle screws each having a head 36 with first and second arms 38, 40 (FIG. 2) defining a receiving channel 42 and a shaft 44 extending from the head 36. The shaft 44 may include threads 46 (FIG. 2) to facilitate securing the first and second vertebral anchors 14, 16 to the respective first and second vertebrae 18, 20. Again, however, the first and second vertebral anchors 14, 16 are merely exemplary in nature. Other types of vertebral anchors (not shown), such as polyaxial pedicle screws, hooks, or other means for engaging the spine, may alternatively be used in the stabilization system 10.

Figure 2:
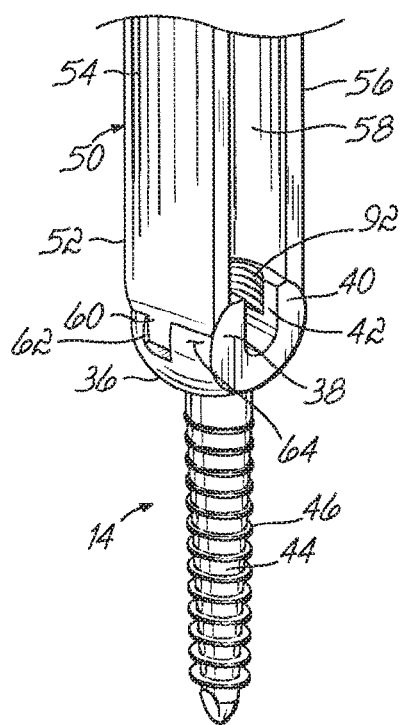
FIG. 2 is a perspective view showing an end of a positioning tool and a vertebral anchor used in the spinal stabilization system of FIG. 1.
Figure 3:
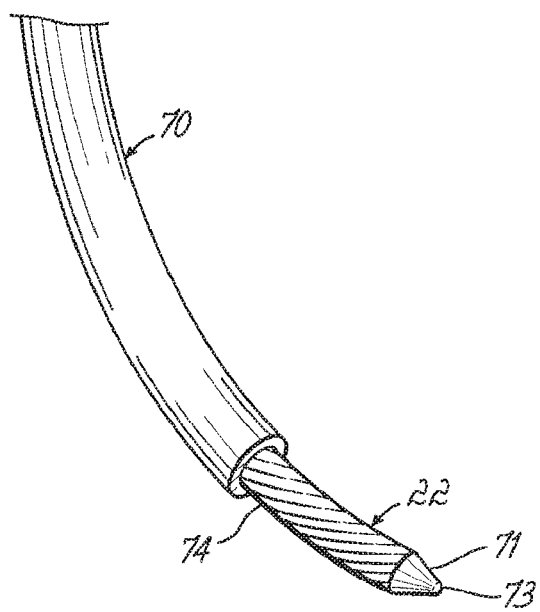
FIG. 3 is a perspective view showing a portion of a delivery device and a connecting element according to one embodiment for use in the spinal stabilization system of FIG. 1.

Now referring to FIGS. 1-3, various components for inserting the stabilization system 10 into the patient's body 12 are shown. Specifically, FIGS. 1 and 2 show a first positioning tool 50 inserted through the first incision 30 and into the patient's body 12 along a path generally toward the first vertebral anchor 14.

In other embodiments, the first positioning tool 50 can be modified to provide for connection of the first positioning tool 50 to the vertebral anchor 14 outside the patient, the first positioning tool 50 and vertebral anchor 14 inserted through the incision 30 as a single unit. In such a configuration, the first positioning tool 50 can be used to guide the vertebral anchor 14 to the vertebral body 18 for securement to the vertebral body. In this embodiment, a k-wire (not shown) that is secured to the vertebral body 18 can be used in connection with a cannulated vertebral anchor 14 to assist in proper securement and positioning of the vertebral anchor 14. This method of securement of vertebral anchors to vertebral bodies may be used for any vertebral anchor used in the stabilization system 10.

The first positioning tool 50 includes a first end 52 that may be coupled to the head 36 of the first vertebral anchor 14 using any suitable technique. In one embodiment, the first positioning tool 50 includes first and second bifurcations 54, 56 defining an elongated slot or cavity 58 there between. The first and second bifurcations 54, 56 are each configured to be received over the respective first and second arms 38, 40 on the head 36 of the first vertebral anchor 14. The first and second bifurcations 54, 56 may also include one or more engagement features designed to mate with a corresponding engagement feature on the head 36. For example, the first and second bifurcations 54, 56 may include a tab or projection 60 configured to be received in a slot 62 formed on an outer surface 64 of the head 36. Other examples of possible arrangements for coupling the first end 52 of first positioning tool 50 to the first vertebral anchor 14 are shown and described in U.S. patent application Ser. Nos. 11/737,151 and 11/743,481, the disclosures of which are fully incorporated herein by reference.

The elongated slot 58 may extend along the entire length of the first positioning tool 50, which may include a handle (not shown) at a location outside the patient's body 12. Alternatively, the elongated slot 58 may only extend across a certain length of the first positioning tool 50. Furthermore, the elongated slot 58 need not extend all the way through the first positioning tool 50. The first positioning tool 50 may therefore have a substantially U-shaped cross section along its length rather than the first and second bifurcations 54, 56.

Although FIG. 1 shows the first vertebral anchor 14 substantially aligned along an axis 68 and the first positioning tool 50 coupled to the first vertebral anchor 14 along the axis 68, the first positioning tool 50 may alternatively be positioned and maintained at an angle relative to the axis 68. For example, FIG. 1 shows the first positioning tool 50 positioned at an angle .theta. to the axis 68. In one embodiment, the angle .theta. is approximately 7.degree. In another embodiment, the angle .theta. is approximately 14.degree. In yet another embodiment, the first positioning tool 50 may be coupled to the first vertebral anchor 14 in a manner that allows the angle .theta. to be adjusted as needed.

FIG. 3 shows a delivery device 70 positioned over the connecting element 22. The delivery device 70 may be made from any type of material suitable for insertion into a patient's body 12. In one embodiment, the delivery device 70 is constructed from flexible polyethylene tubing having a rigidity greater than that of the connecting element 22. In other embodiments, the delivery device 70 may be constructed from materials such as metal to provide even greater rigidity. Although the delivery device 70 is shown as being a tubular element, other configurations are possible in which the delivery device 70 does not entirely surround the connecting element 22. For example, the delivery device 70 may alternatively be a helical element (not shown) or some other structure extending over a length of the connecting element 22 to provide added rigidity for reasons discussed below. Additionally, the delivery device 70 may comprise multiple component parts assembled together from the same or a variety of different materials.

In some embodiments, the connecting element 22 may be provided with an end portion 71 that is more rigid than the remainder of the connecting element 22. This may be achieved by constructing the connecting element 22 with different material properties at the end portion 71 or by mounting a separate component to the connecting element 22. For example, as shown in FIG. 3, the end portion 71 may be a bullet-shaped nose or similar structure coupled to the connecting element 22. The nose may be constructed of metal or other rigid material and may be tapered to a tip 73 to facilitate movement through tissue. The material of the end portion 71 may also be selected to help identify the location of the end portion 71 as the connecting element 22 is advanced through tissue. For example, the end portion 71 may be constructed from radiopaque material so as to serve as a marker during a surgical procedure.

With reference to FIGS. 3A-3G, a method of inserting the stabilization system 10 into the patient's body 12 will now be described. After inserting the first and second vertebral anchors 14, 16 into the patient's body 12, the connecting element 22 may be positioned relative to the first and second vertebral anchors 14, 16 using the first positioning tool 50 and delivery device 70. Specifically, the first positioning tool 50 may be inserted through the first incision 30 and coupled to the head 36 of the first vertebral anchor 14 in the manner discussed above. The delivery device 70, which is at least partially positioned over the connecting element 22, may then be inserted through the first incision 30 and along at least a portion of the first positioning tool 50.

Figure 3A:
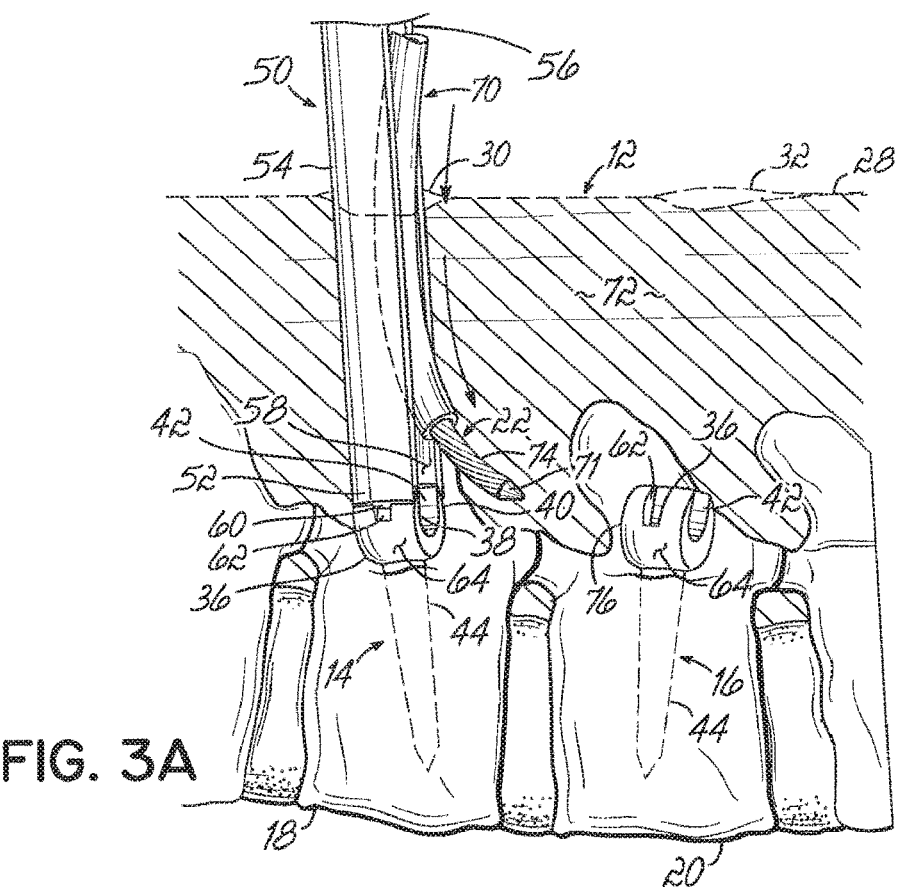
FIGS. 3A-3G are schematic views sequentially illustrating one method of inserting a flexible spinal stabilization system into a patient.

The delivery device 70 may have a width smaller or larger than the width of the elongated slot 58. In either embodiment, the first positioning tool 50 facilitates directing the delivery device 70 generally toward the second vertebral anchor 16. For example, FIG. 3A shows the delivery device 70 having a diameter smaller than the width of the elongated slot 58 so that the delivery device 70 may be received within the elongated slot 58. Such an arrangement enables the delivery device 70 to be inserted into the patient's body 12 through the same channel established by the first positioning tool 50. Additionally, the elongated slot 58 in such an embodiment may be provided with an engagement feature (not shown) configured to cooperate with a mating engagement feature (not shown) on the delivery device 70. The engagement features may be, for example, a tongue provided in the elongated slot 58 and a mating groove or track provided on the outer surface of the delivery device 70. Alternatively, the delivery device 70 may be provided with a tongue and the elongated slot 58 may be provided with a groove or track. Such engagement features help guide the delivery device 70 along a desired path through elongated slot 58 so that the delivery device 70 is ultimately directed toward the second vertebral anchor 16.

Figure 4:
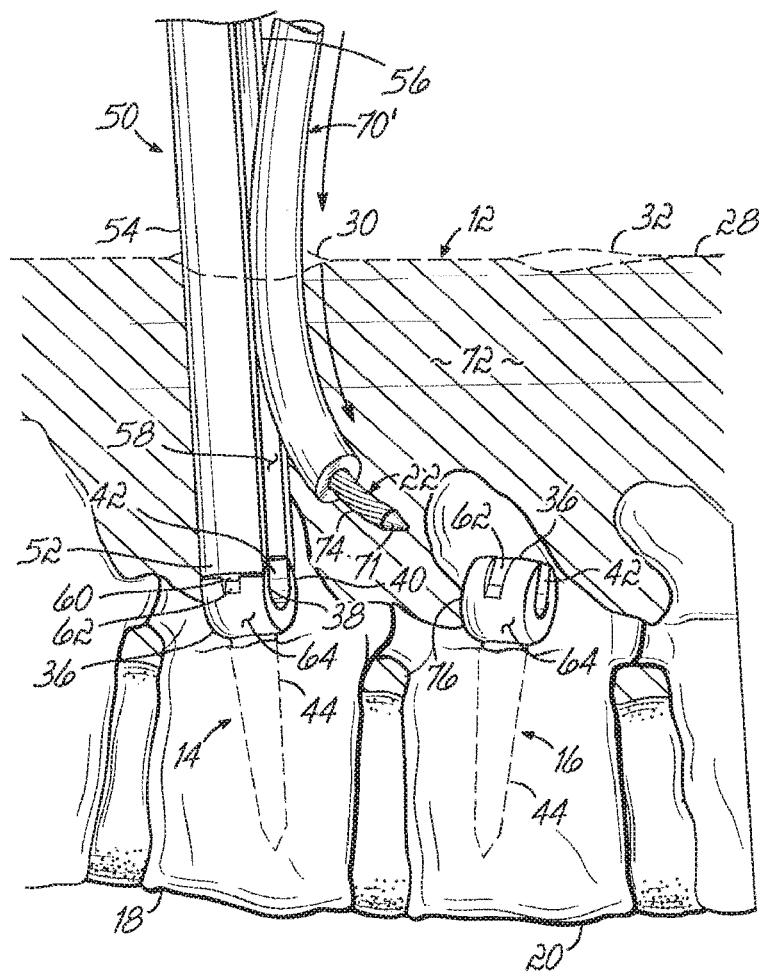
FIG. 4 is a schematic view similar to FIG. 3A showing a delivery device according to an alternative embodiment.

If the delivery device 70 has a diameter slightly larger than the width of the elongated slot 58, the delivery device 70 may still be partially received in the elongated slot 58. FIG. 4 shows one example of such an embodiment, with prime (') marks being used to designate structure that slightly differs from FIG. 3A. A surgeon may slide the delivery device 70' along the first positioning tool 50 to facilitate directing the delivery device 70' generally toward the second vertebral anchor 16. For example, the delivery device 70' may be formed with a desired degree of curvature. By using the first positioning tool 50 for guidance and/or leverage, the surgeon can guide the delivery device 70' along a path corresponding to its curvature.

Regardless of how the first positioning tool 50 facilitates directing the delivery device 70 (or 70') generally toward the second vertebral anchor 16, the strength of the delivery device 70 and its ability to withstand compression forces enables it to be advanced through tissue 72 in the patient's body 12 without being significantly deflected. A first portion 74 of the connecting element 22 may remain exposed when the connecting element 22 is inserted with the delivery device 70, but does not extend an appreciable distance so that the connecting element 22 does not adversely affect the insertion of the delivery device 70 through the tissue 72. Indeed, when the end portion 71 is in the form of a bullet-shaped nose (as shown), the shape and rigidity of the nose may facilitate movement of the connecting element 22 through the tissue 72.

Figure 3B:
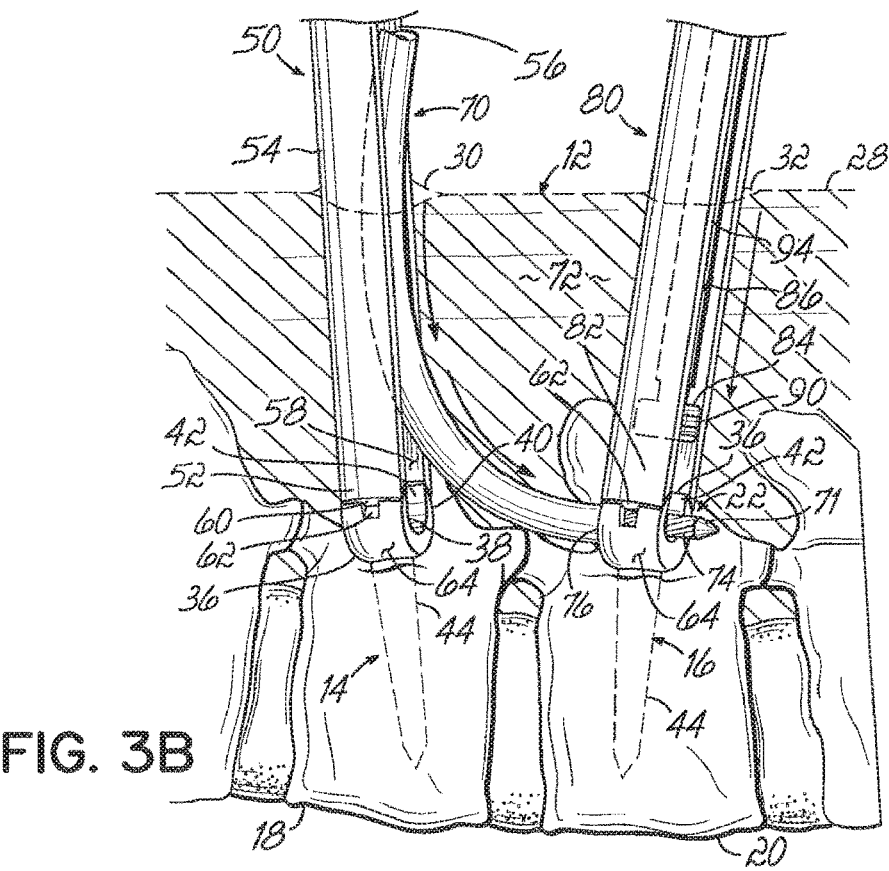

The delivery device 70 may be manipulated while being advanced along the first positioning tool 50 until the first portion 74 of the connecting element 22 is received in or near the receiving channel 42 of the second vertebral anchor 16, as shown in FIG. 3B. To this end, the delivery device 70 may be passed through the first incision 30 and directed toward the second vertebral anchor 16 until it abuts and/or confronts a generally flat surface 76 defined by the head 36. If the first portion 74 of the connecting element 22 remains exposed during this insertion, the first portion 74 may be received in the receiving channel 42 of the second vertebral anchor 16 without additional steps. If the delivery device 70 is positioned over the first portion 74 during insertion, the connecting element 22 may then be pushed through the delivery device 70 until the first portion 74 extends through the receiving channel 42.

Alternatively, the delivery device 70 may be constructed from a flexible shape memory material, such as Nitinol. The shape memory material may be temperature-dependent such that the delivery device 70 has a normally straight configuration at room temperature, but assumes a curved configuration once placed within the patient's body 12 (where it is exposed to body temperatures). The delivery device 70 may still be passed through the patient's body 12 and directed generally toward the second vertebral anchor 16 while using the first positioning tool 50 for guidance and/or leverage.

In some instances, the delivery device 70 may not be directly aligned with the receiving channel 42 after directing the connecting element 22 toward the second vertebral anchor 16. If necessary or desired, additional tools (not shown) may be inserted through the second incision 32 to help properly position the first portion 74 within the receiving channel 42. Because the receiving channel 42 is open, the first portion 74 may be easily received by the second vertebral anchor 16 in a top-loading fashion. Radiographic images can be obtained to determine the proper positioning of the first portion 74 of the connecting element 22. The end portion 71 can be formed of a material that facilitates the identification of the proper placement of the connecting element 22.

Before or after the first portion 74 of the connecting element 22 is received in the receiving channel 42, a second positioning tool 80 may be inserted through the second incision 32 and along a path generally toward the second vertebral anchor 16. The second positioning tool 80 includes a second end 82 configured to be coupled to the head 36 of the second vertebral anchor 16 in the same manner as the first end 52 of the first positioning tool 50 and the head 36 of the first vertebral anchor 14. A fastener 84 may then be passed through the second incision 32 and percutaneously delivered to the receiving channel 42. For example, the fastener 84 may be delivered through an elongated slot 86 defined in the second positioning tool 80, as shown in FIG. 3B. The fastener 84 is secured within the receiving channel 42 so that the first portion 74 of the connecting element 22 is retained (e.g., compressed) between the fastener 84 and the second vertebral anchor 16.

Figure 3C:
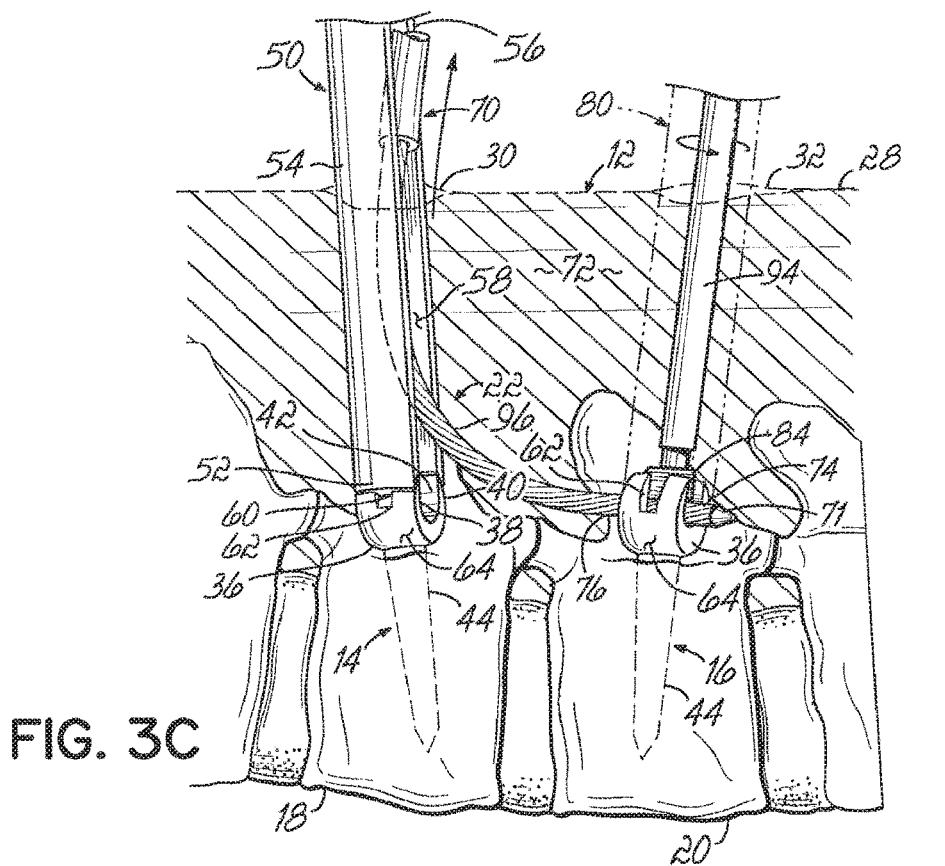

In one embodiment, the fastener 84 is a set screw having external threads go that engage internal threads 92 (FIG. 2) provided in the receiving channel 42 of the second vertebral anchor 16. The fastener 84 may be delivered through the second positioning tool 80 and tightened using a driving tool 94, as shown in FIG. 3C (with the second positioning tool 80 shown in phantom for clarity). The second positioning tool 80 stabilizes the second vertebral anchor 16 as the set screw is rotated to engage the internal threads 92. Thus, the second positioning tool 80 may serve as an anti-torque instrument to counteract the forces applied by the driving tool 94. In other embodiments, the first portion 74 of the connecting element 22 may be secured to the head 36 of the second vertebral anchor 16 using different types of fasteners or other elements. For example, the second vertebral anchor 16 may alternatively be shaped to cooperate with a cap (not shown) for retaining the first portion 74 of the connecting element 22.

Once the first portion 74 of the connecting element 22 is secured to the second vertebral anchor 16, the second positioning tool 80 may be removed from the patient's body 12 through the second incision 32. The delivery device 70 may also be removed from the connecting element 22 to expose a second portion 96 of the connecting element 22. As shown in FIG. 3C, the delivery device 70 is removed through the first incision 30 in the patient's skin 28. The tissue 72 surrounding the connecting element 22 effectively maintains the connecting element 22 in position while the delivery device 70 is removed.

Figure 3D:
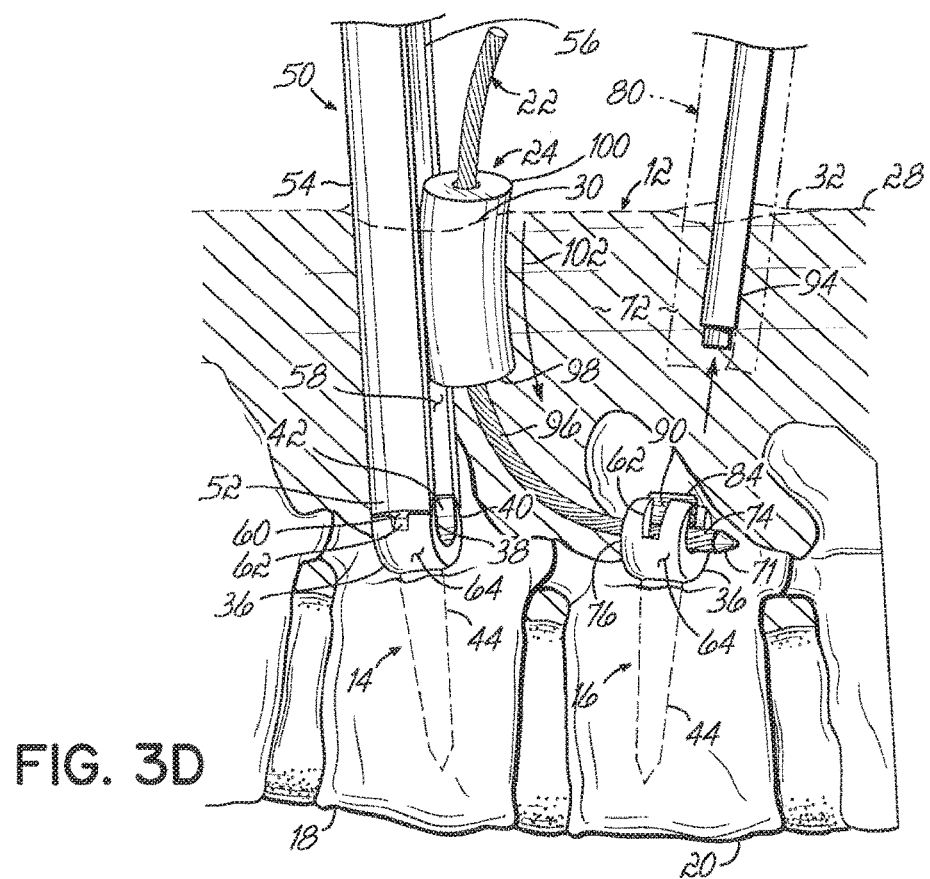

FIG. 3D illustrates the spacer 24 being advanced through the first incision 30 and over the connecting element 22. The second positioning tool 80 and driving tool 94 may be removed before or after the spacer 24 is advanced. Additionally, although the first positioning tool 50 is shown as remaining within the patient's body 12, it will be appreciated that the first positioning tool 50 may alternatively be removed through the first incision 30 prior to this step as well. The spacer 24 may be advanced along the length of the connecting element 22 until a first end 98 of the spacer 24 confronts the generally flat surface 76 of the head 36. If desired, a pushing instrument (not shown) may be used to aid in movement of the spacer 24 through tissue 72 and along the connecting element 22. The pushing instrument may be inserted through the first incision 30 and adapted to engage a second end 100 of the spacer 24 to push the spacer 24 generally in the direction of arrow 102. Alternatively or additionally, the pushing instrument may be adapted to engage a portion of the spacer 24 between the first and second ends 98, 100 to adjust the orientation of the spacer 24 relative to the first vertebral anchor 14 and/or second vertebral anchor 16. In such an embodiment, the pushing instrument may be inserted through a separate incision (not shown) or the second incision 32.

Prior to insertion of the spacer 24, the surgeon can determine the distance between vertebral anchors 14, 16 and size the spacer 24 outside the patient to a length that achieves a desired patient outcome. For example, if the surgeon hopes to achieve posterior distraction between vertebrae, the spacer 24 can be sized greater than the distance between opposing surfaces of the vertebral anchors 14, 16 upon which the spacer 24 engages. This measurement may be made, for example and without limitation, based on the distance outside the patient between instruments engaging the anchors or through radiographic means.

Figure 3E:
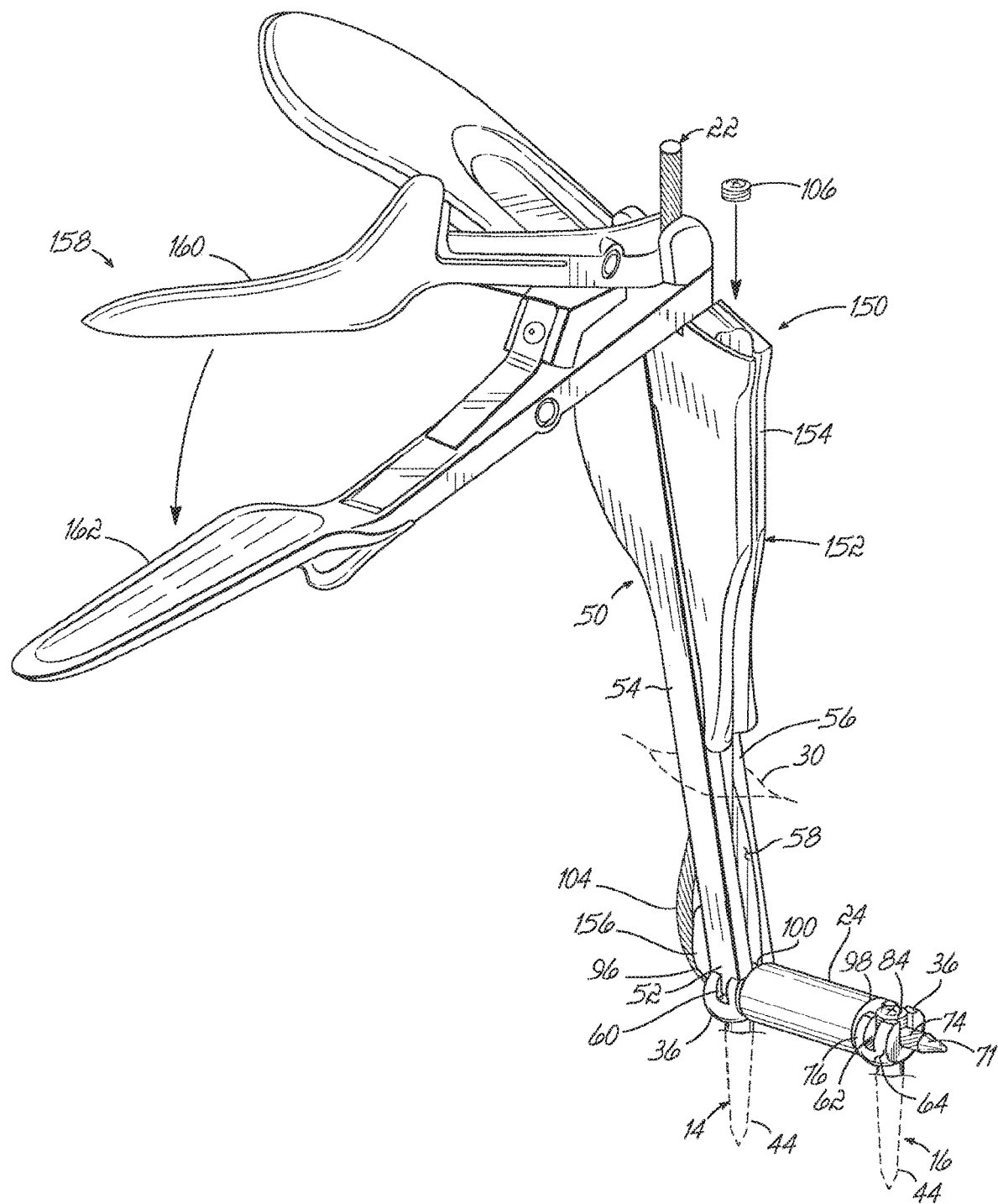

After the spacer 24 has been advanced along the connecting element 22, the second portion 96 of the connecting element 22 may extend generally toward the first incision 30 before being received in the receiving channel 42 of the first vertebral anchor 14 or the elongated slot 58 of the first positioning tool 50. The second portion 96 of the connecting element 22 may therefore be moved to a desired position relative to the first vertebral anchor 14 by manipulating the connecting element 22 by hand or by using one or more additional tools. For example, as shown in FIG. 3E, a tensioning tool 150 configured to cooperate with the first positioning tool 50 may be inserted through the first incision 30. The tensioning tool 150 includes a stabilizing element 152 having a top portion 154 aligned generally above the second end 100 of the spacer 24. A bottom portion 156 of the tensioning tool 150 may be inserted through the elongated slot 58 to an opposite side of the first positioning tool 50 to direct the second portion 96 of the connecting element 22 into the receiving channel 42 (FIG. 2) of the first vertebral anchor 14. When the second portion 96 is received in the receiving channel 42, the spacer 24 is properly positioned between the first and second vertebral anchors 14, 16.

Additional length 104 of the connecting element 22 extending from the second portion 96 may curve upwardly and around the bottom portion 156 of the stabilizing element 152 so as to extend into the elongated slot 58 of the first positioning tool 50.

Figure 3F:
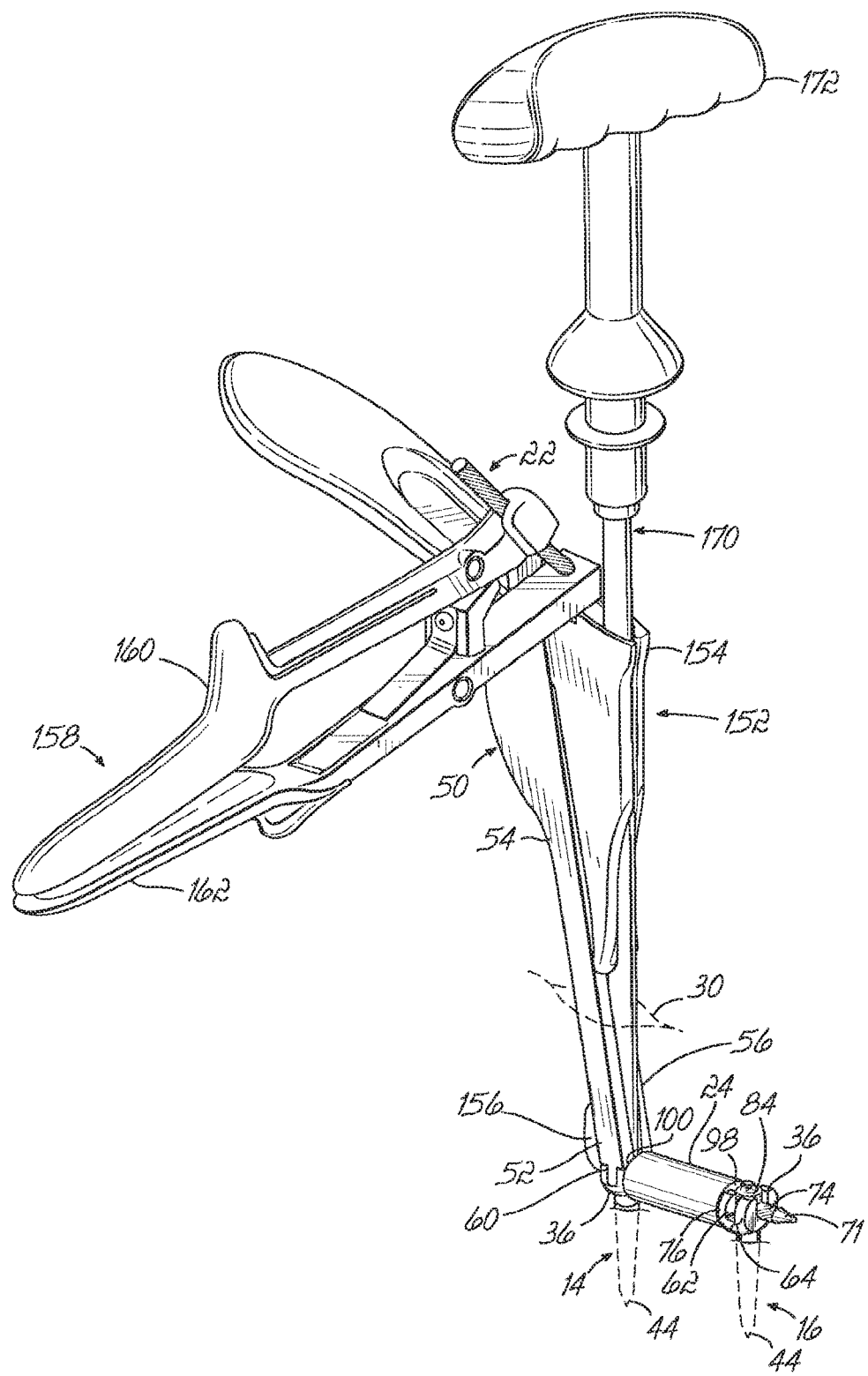
Figure 3G:
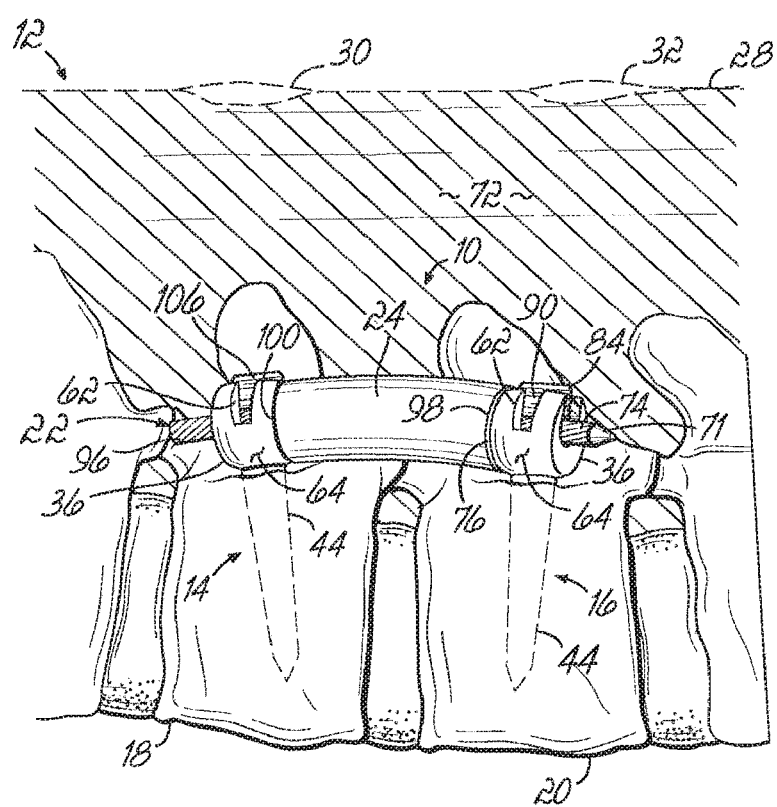

Indeed, the additional length may continue to extend out of the elongated slot 58 and through the top portion 154 of the stabilizing element 152. While maintaining the bottom portion 156 of the stabilizing element 152 in position (so that the second portion 96 of the connecting element 22 is maintained in the receiving channel 42), the additional length 104 may be pulled to place the connecting element 22 in tension. The additional length 104 may be pulled manually by hand or by using a surgical tool. In one embodiment, the tensioning tool 150 further includes a gripping element 158 having a first arm 160 configured to clamp or otherwise securely grip the connecting element 22 after the additional length 104 extends through the stabilizing element 152. As shown in FIGS. 3E and 3F, a surgeon may pivot the first arm 160 relative to a second arm 162 of the gripping element 158 to mechanically pull the connecting element 22 through the stabilizing element 152.

Once the connecting element 22 is placed under a desired degree of tension, the second portion 96 is secured to the first vertebral anchor 14. The second portion 96 may be secured in a manner similar to the first portion 74. To this end, a fastener 106, such as a set screw, may be inserted through the first incision 30 and percutaneously delivered to the receiving channel 42 of the first vertebral anchor 14. More specifically, the fastener 106 may be delivered through the stabilizing element 152 and first positioning tool 50 using a driving tool 170, which may be similar to the driving tool 94 (FIG. 3C). A handle 172 of the driving tool 170 is rotated to drive the fastener 106 into engagement with the internal threads 92 (FIG. 2) provided in the receiving channel 42. The threaded engagement secures the second portion 96 of the connecting element 22 relative to the first vertebral anchor 14. The connecting element 22 may then be cut proximate the first vertebral anchor 14, and the first positioning tool 50 and the tensioning tool 150 may be removed from the patient's body 12 through the first incision 30. This results in the arrangement shown in FIG. 3G.

Figure 5:
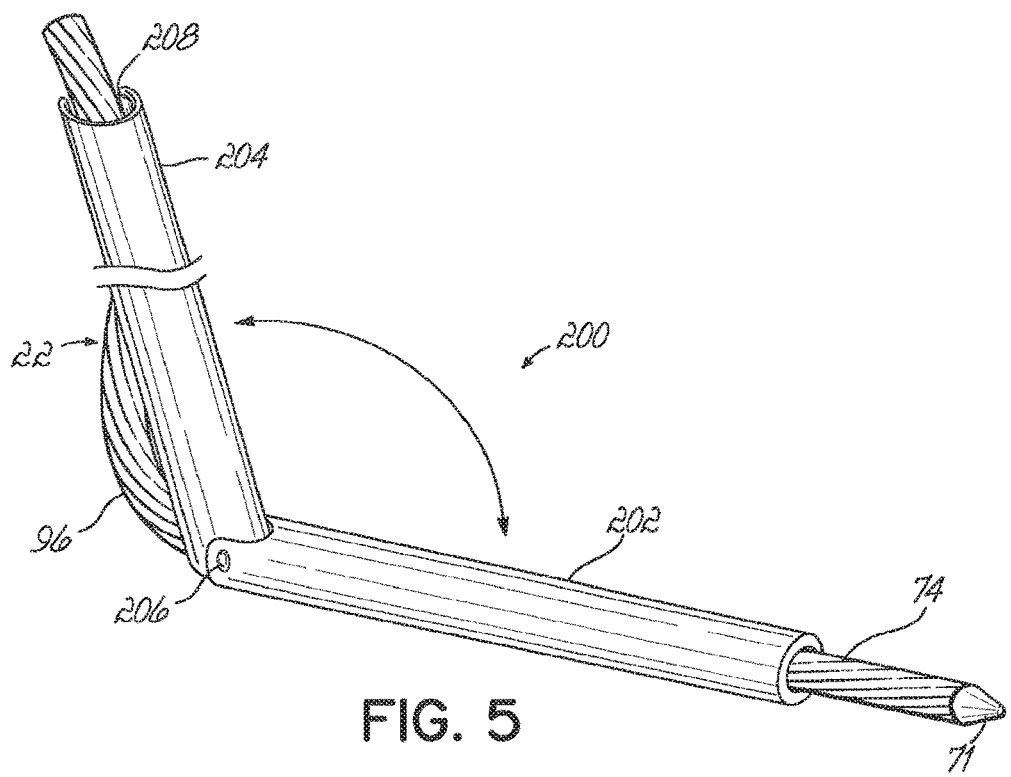
FIG. 5 is a perspective view of a delivery device and a connecting element according to another embodiment for use in the spinal stabilization system of FIG. 1.

FIG. 5 shows a delivery device 200 according to an alternative embodiment. The delivery device 200 includes a first sheath member 202 coupled to a second sheath member 204 at an articulating joint 206. In the illustrative embodiment shown in FIG. 5, the first sheath member 202 is hollow so that it may be positioned over the connecting element 22 in the same manner as the delivery device 70 (FIG. 3). The second sheath member 204 may also be hollow, and may further include a slot 208 for accommodating the connecting element 22. Alternatively, the second sheath member 204 may be solid so that the connecting element 22 may only extend through the first sheath member 202.

Because of the articulating joint 206, the first sheath member 202 may pivot relative to the second sheath member 204 to change the angle defined between the two components. In one embodiment, the articulating joint 206 may be configured to lock the first sheath member 202 at several different angles relative to the second sheath member 204. Any suitable locking technique may be used. For example, in a manner not shown herein, the articulating joint 206 may include a ratcheting mechanism, locking pin, or other structure capable of locking the first sheath member 202 at one or more angles relative to the second sheath member 204. In addition to this ability to adjust angular orientation, the first sheath member 202 may be designed to have an adjustable length. For example, the first sheath member 202 may include telescoping or extendable sections (not shown).

Figure 5A:
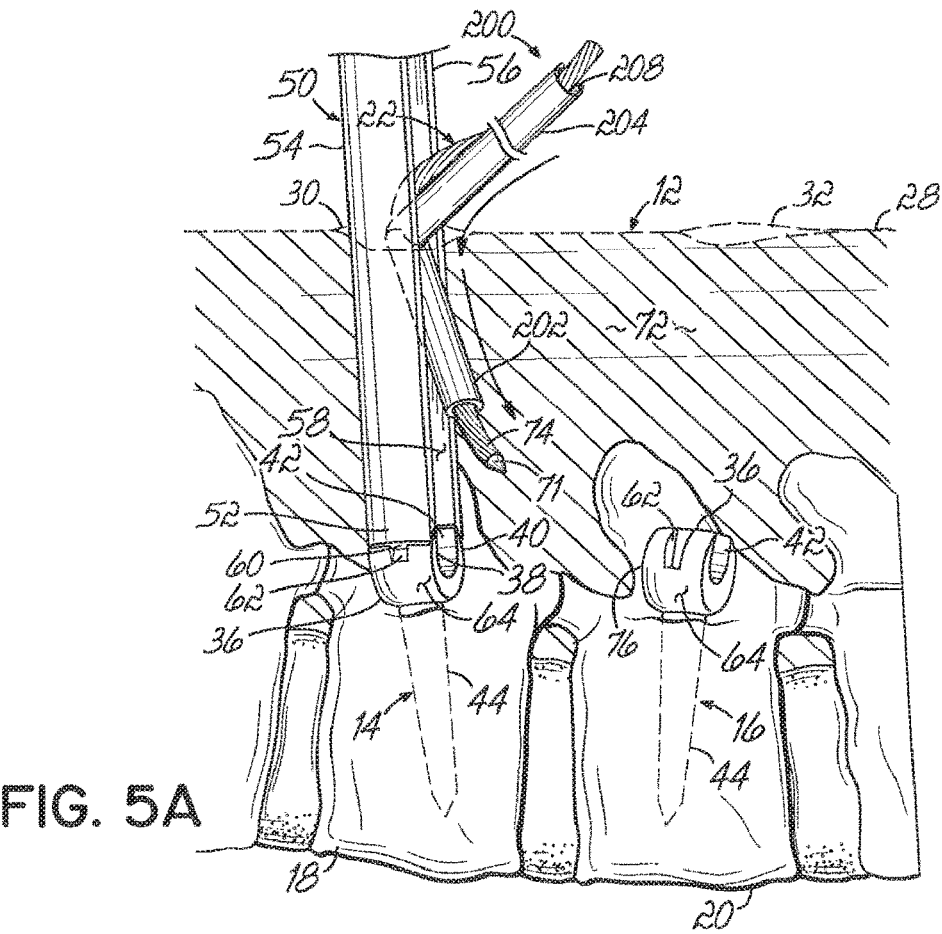
FIGS. 5A-5C are schematic views sequentially illustrating another method of inserting a flexible spinal stabilization system into a patient.
Figure 5B:
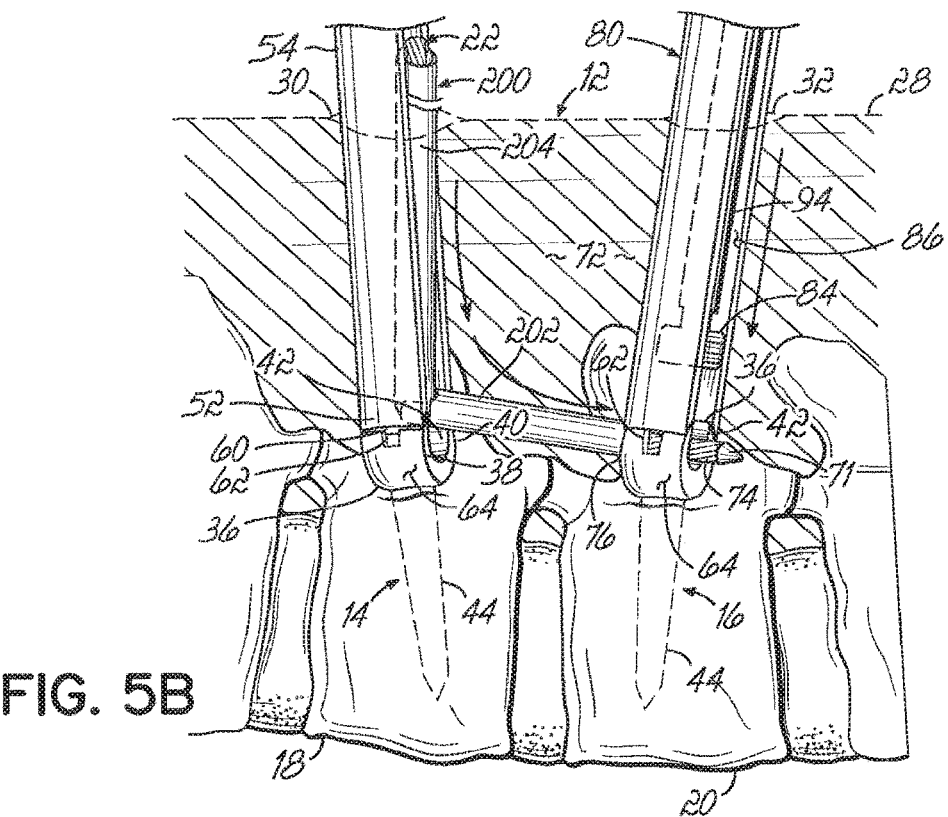
Figure 5C:
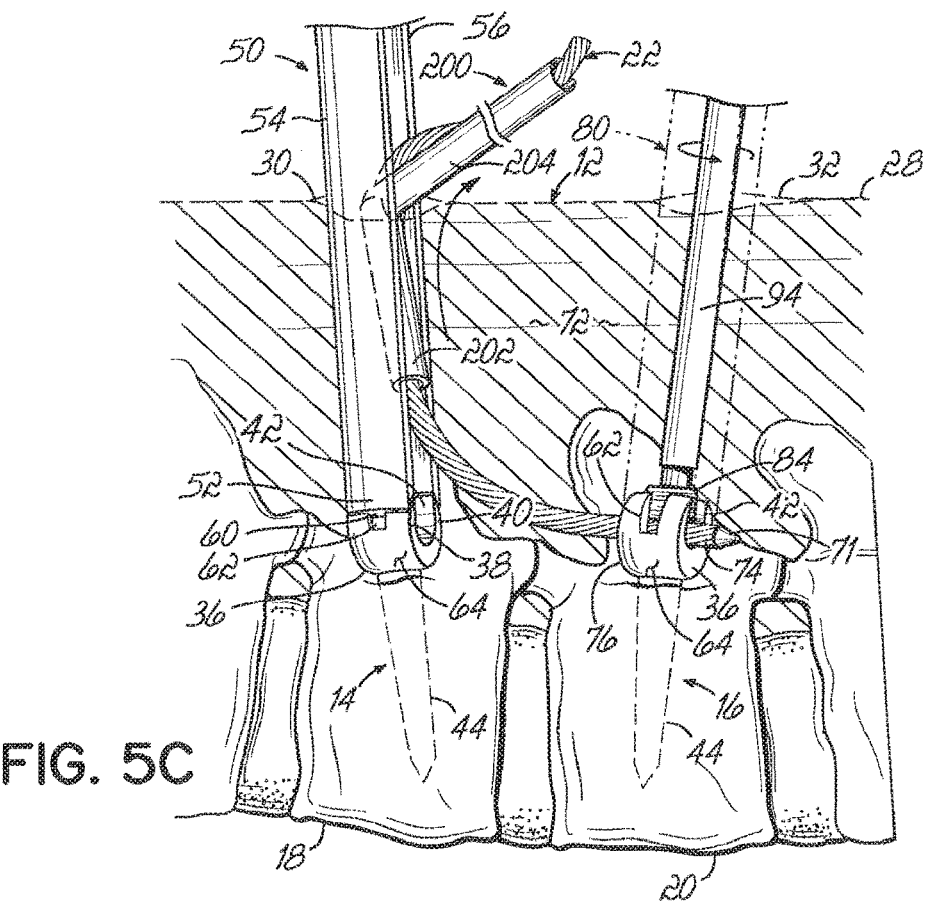

FIGS. 5A-5C illustrate the delivery device 200 being used to deliver the connecting element 22 to within the patient's body 12, with like reference numbers being used to refer to like structure from FIGS. 3A-3G. The delivery device 200 may be inserted through the first incision 30 within or near the first positioning tool 50. Additionally, the first sheath member 202 and/or second sheath member 204 may be at least partially received in the elongated slot 58 of the first positioning tool 50 to help guide the first sheath member 202 generally toward the second vertebral anchor 16. Although FIGS. 5A-5C illustrate the first sheath member 202 and second sheath member 204 having diameters smaller than the width of the elongated slot 58, those skilled in the art will appreciate that the diameters may alternatively be greater than the width of the elongated slot 58. To this end, the delivery device 200 may be used in a manner similar to the delivery device 70 (FIG. 3A) or the delivery device 70' (FIG. 4) depending on the diameters of the first sheath member 202 and second sheath member 204.

Although the techniques discussed above for guiding the delivery devices 70, 70' may still apply (engagement features, using the first positioning tool 50 for leverage, etc.), the delivery device 200 is manipulated differently when passed through the first incision 30. This difference is due to the first sheath member 202 being positioned at an angle relative to the second sheath member 204 (by means of the articulating joint 206). In some instances it may be easier to use the delivery device 200 to delivery the first portion 74 of the connecting element 22 to the second vertebral anchor 16, whereas in other instances it may be easier to use the delivery device 70. Note that the angle of the first sheath member 202 relative to the second sheath member 204 may be adjusted one or more times during the insertion of the delivery device 200. Alternatively, the angle may be adjusted prior to insertion and maintained throughout the procedure.

After using the delivery device 200 to deliver the first portion 74 of the connecting element 22 to the second vertebral anchor 16, the first portion 74 may be secured to the second vertebral anchor 16 in the same manner discussed above with reference to FIG. 3C. The delivery device 200 may then be removed from the patient's body 12 by retracting it back through the first incision 30 and over the connecting element 22. As with the insertion procedure, the angle of the first sheath member 202 relative to the second sheath member 204 may be adjusted before or during this removal procedure. After the delivery device 200 is removed, the spacer 24 may be advanced over the connecting element 22 and the second portion 96 may be secured to the first vertebral anchor 14, as discussed above with reference to FIGS. 3D-3G.

Figure 6A:
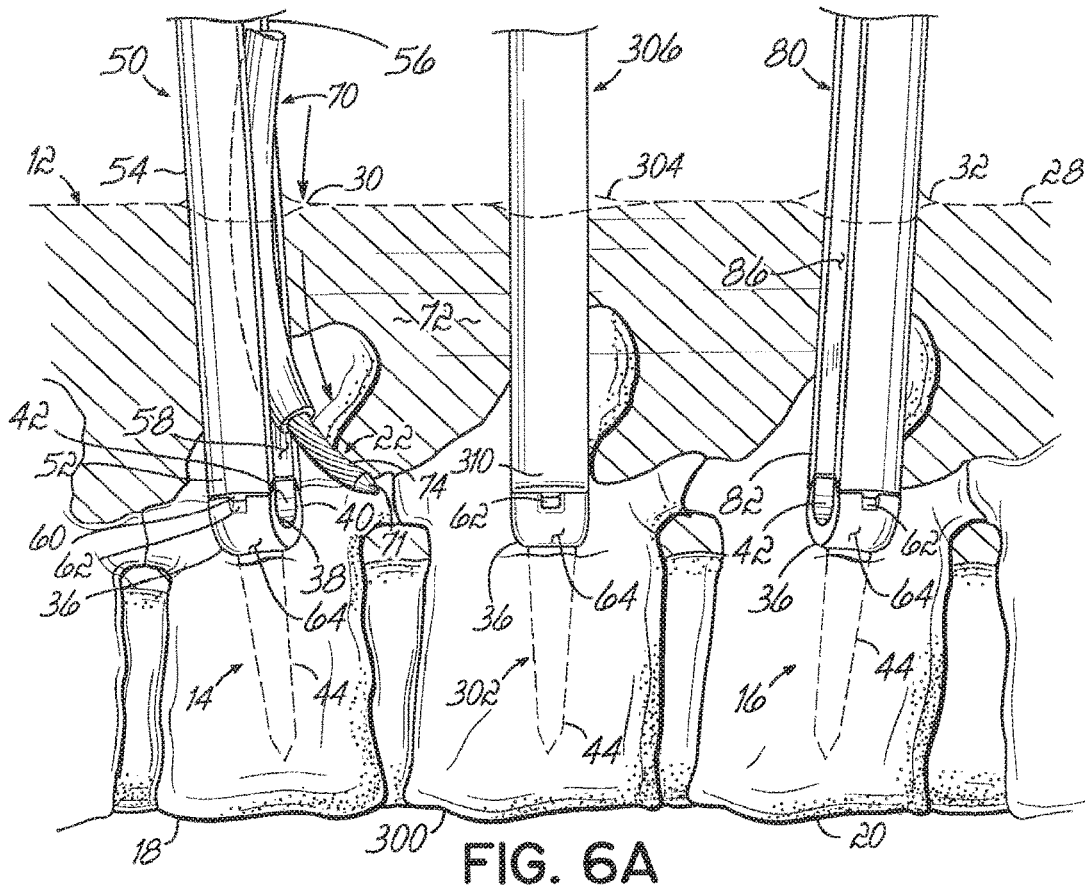
FIGS. 6A-6C are schematic views sequentially illustrating yet another method of inserting a flexible spinal stabilization system into a patient.
Figure 6B:
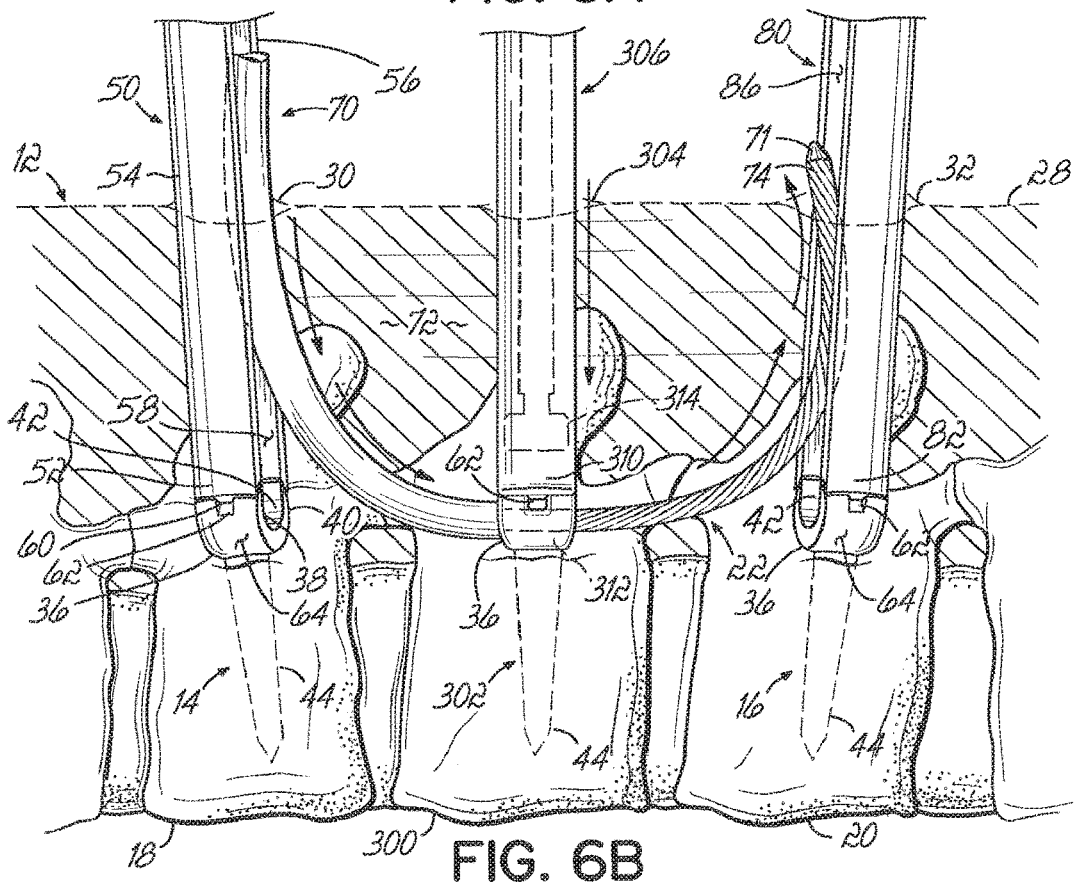
Figure 6C:
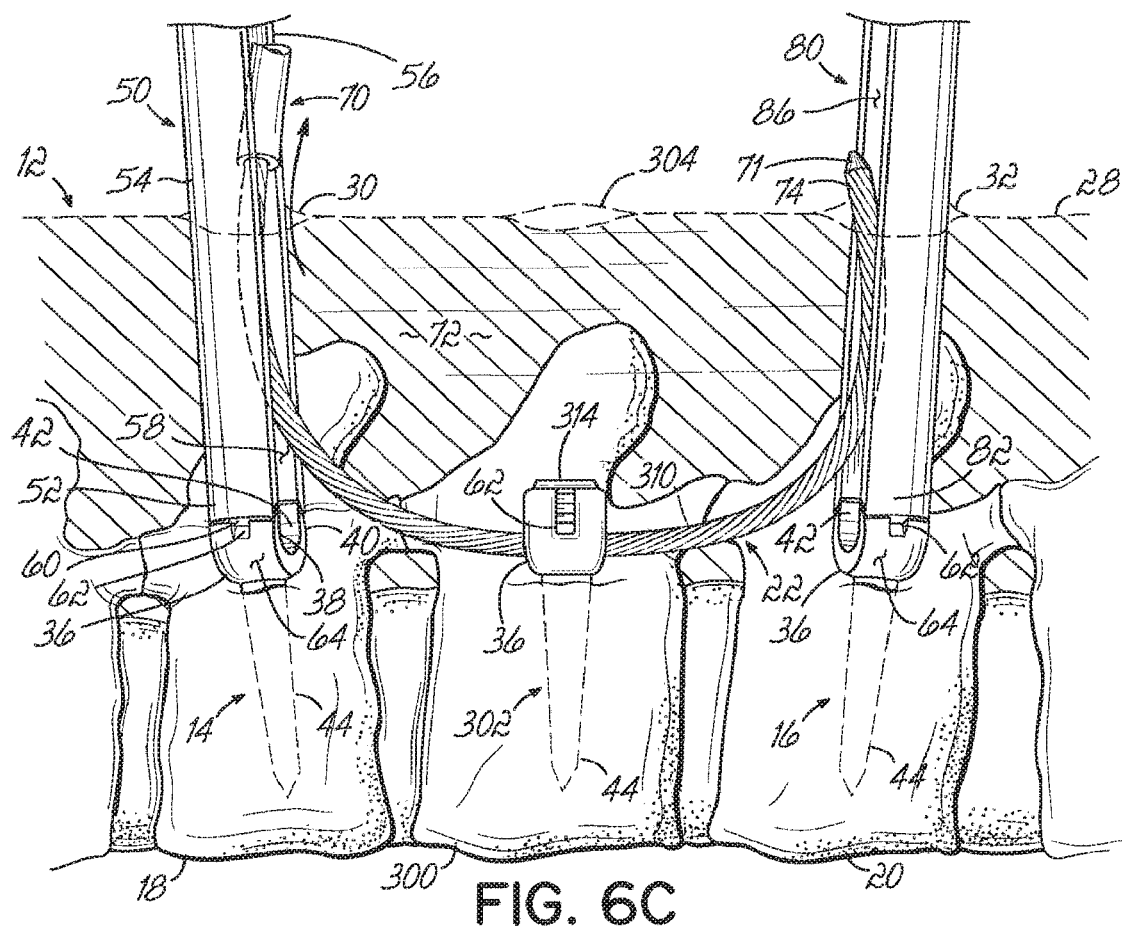

The embodiments described above relate to using the stabilization system 10 as part of a single-level treatment (i.e., between two adjacent vertebrae). However, it will be appreciated that the same techniques and tools may be used as part of a multi-level treatment as well. For example, FIGS. 6A-6C illustrate a third vertebra 300 positioned between the first and second vertebrae 18, 20 and a method of installing a stabilization system to effect treatment across the first, second, and third vertebrae 18, 20, 300. Because the techniques and tools are similar to those discussed above with reference to FIGS. 3A-3G, like reference numbers are used to refer to like structure.

In this embodiment, a third vertebral anchor 302 may be inserted through a third incision 304 at a third location on the patient's skin 28 and ultimately secured to the third vertebra 300 using conventional techniques. A third positioning tool 306 may then be inserted through the third incision 304 and generally toward the third vertebral anchor 302. The third vertebral anchor 302 may be a pedicle screw having substantially the same construction as the first and second vertebral anchors 14, 16, and the third positioning tool 306 may have substantially the same construction as the first and second positioning tools 50, 80. To this end, the third positioning tool 306 may include an elongated slot or cavity (not shown). Additionally, a third end 310 of the third positioning tool 306 may be coupled to the head 36 of the third vertebral anchor 302 using the techniques discussed above with reference to the first and second positioning tools 50, 80.

After the first, second, and third positioning tools 50, 80, 306 are coupled to the first, second, and third vertebral anchors 14, 16, 302, respectively, the delivery device 70 and connecting element 22 may be inserted through the first incision 30. The first positioning tool 50 is used to facilitate directing the delivery device 70 generally toward the third vertebral anchor 302. Once the delivery device 70 contacts the head 36 of the third vertebral anchor 302 or the third positioning tool 306, the connecting element 22 may be pushed through the delivery device 70 so that a third portion 312 (located between the first portion 74 and second portion 96) extends through the receiving channel 42 (FIG. 2) in the third vertebral anchor 302 or through the elongated slot of the third positioning tool 306. In some embodiments, the connecting element 22 may have a preformed curvature so that it curves upwardly and generally toward the second incision 32 when further pushed through the delivery device 70. The first portion 74 may be received in the elongated slot 86 and/or ultimately exit the patient's body 12 through the second incision 32. In other embodiments, the connecting element 22 approaches the second vertebral anchor 16 when further pushed through the delivery device 70. The first portion 74 may then be received in the elongate slot 86 and pulled up through the second incision 32.

Once the connecting element 22 is pushed sufficiently through the delivery device 70, the third portion 312 may be secured to the third vertebral anchor 302 using any suitable technique. For example, the third portion 312 may be retained in the receiving channel 42 (FIG. 2) of the third vertebral anchor 302 by passing a fastener 314, such as a set screw, through the elongated slot or cavity of the third positioning tool 306 and securing the fastener 314 within the receiving channel 42 over the third portion 312. The delivery device 70 may then be pulled back through the first incision 30 and removed from the connecting element 22 so as to expose the second portion 96. At this point, the third portion 312 is secured within the patient's body 12 whereas the first and second portions 74, 96 are positioned in or proximate the elongated slots 58, 86, respectively. Such an arrangement allows spacers, like spacer 24, to be placed over the connecting element 22 and for the first and second portions 74, 96 to be secured to the first and second vertebral anchors 14, 16 using the techniques described above. For example, the tensioning tool 150 (FIGS. 3E and 3F) and fastener 106 may be used to secure the second portion 96 to the first vertebral anchor 14, and the tensioning tool 150 and fastener 84 may be used to secure the first portion 74 to the second vertebral anchor 16. Any additional length of the connecting element 22 extending beyond the first and second portions 74, 96 may be cut proximate the first and second vertebral anchors 14, 16 to complete the installation procedure.

In one embodiment, the surgeon can be provided with several spacers each having different elastic characteristics for the multi-level construct shown in FIGS. 6A-6C. The surgeon can choose the spacer, like spacer 24, based on the patient's condition and include spacers having different elastic characteristics in a single patient, if desired. For example, the spacer between anchors 14 and 302 can be a more elastic material and the spacer between anchors 302 and 16 can be a more rigid material.

In another embodiment, the surgeon can be provided a single connecting element that has varying elastic characteristics over its length for the multi-level construct shown in FIGS. 6A-6C. The surgeon may then implant the elastically varied connecting element in a desired location to provide a desired result in the patient. For example, the elastically varied connecting element can include radiographic markers that assist the surgeon in identifying the differing areas of elasticity when the connecting element is implanted in the patient to provide differing characteristics of the stabilization system 10 at adjacent levels.

Figure 7A:
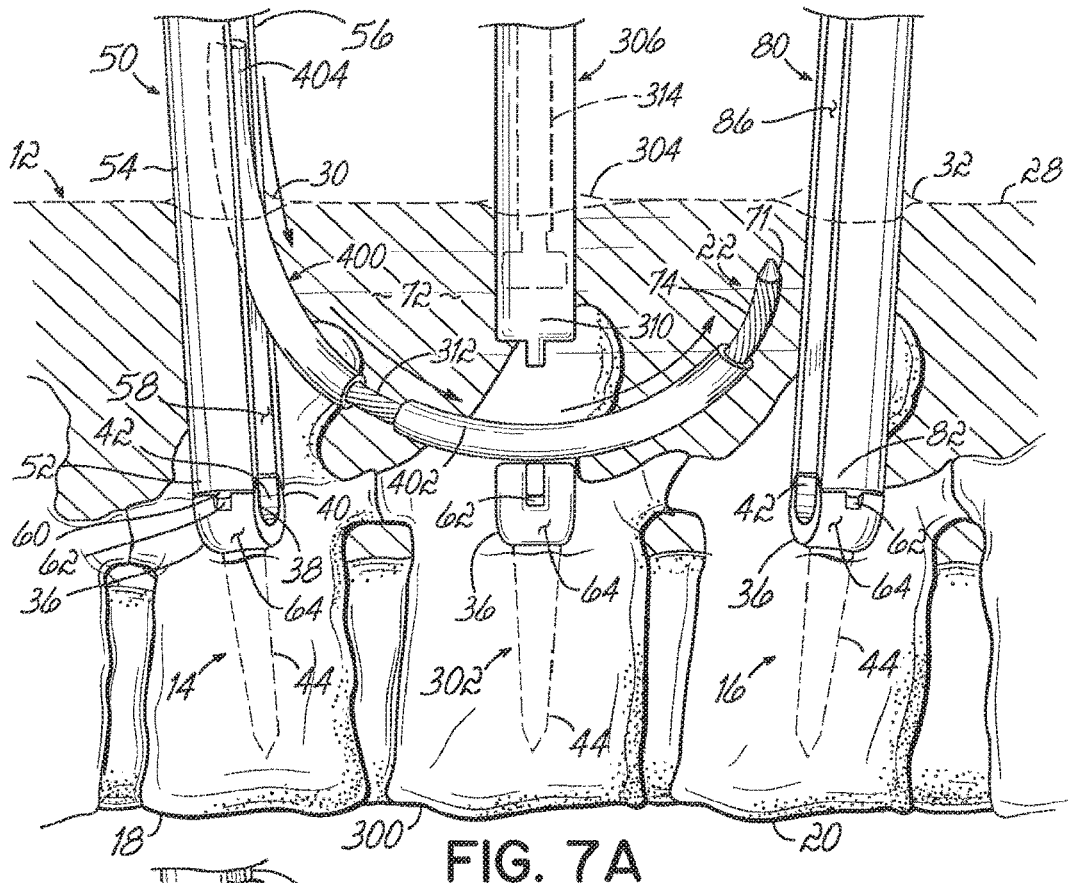
FIGS. 7A-7C are schematic views sequentially illustrating yet another method of inserting a flexible spinal stabilization system into a patient.
Figure 7B:
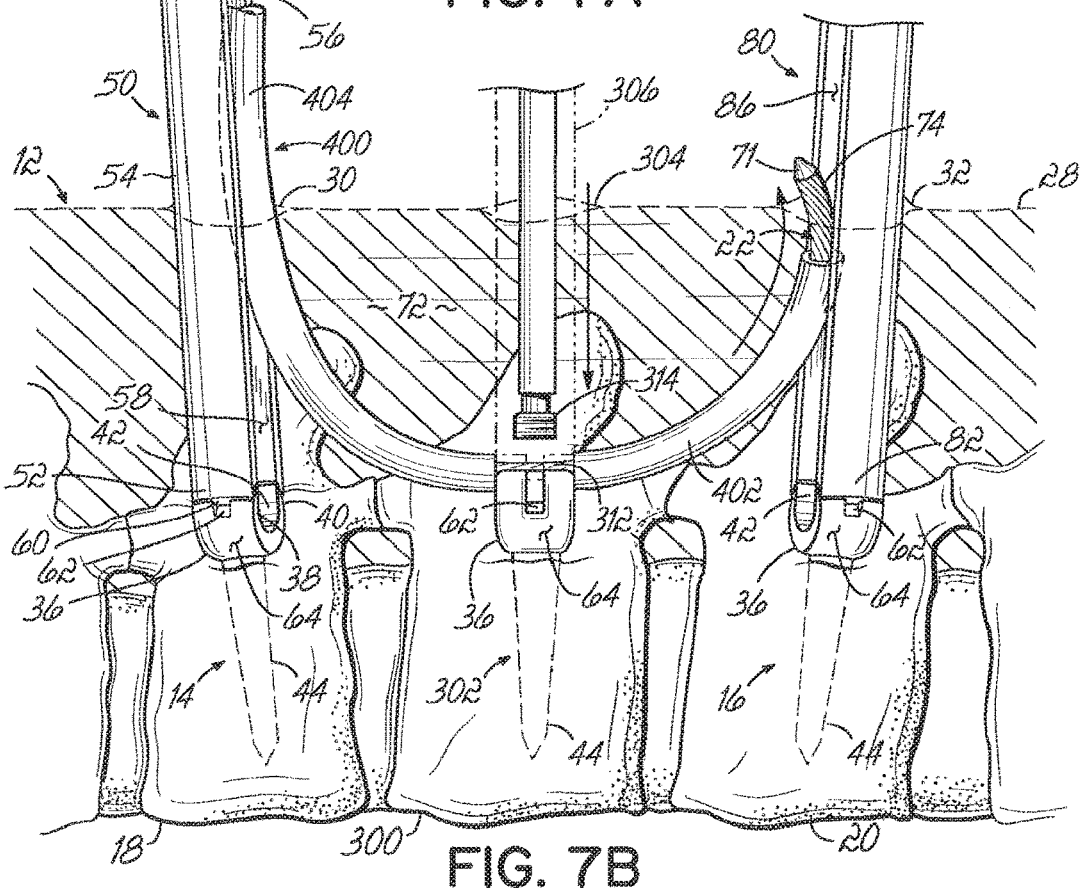
Figure 7C:
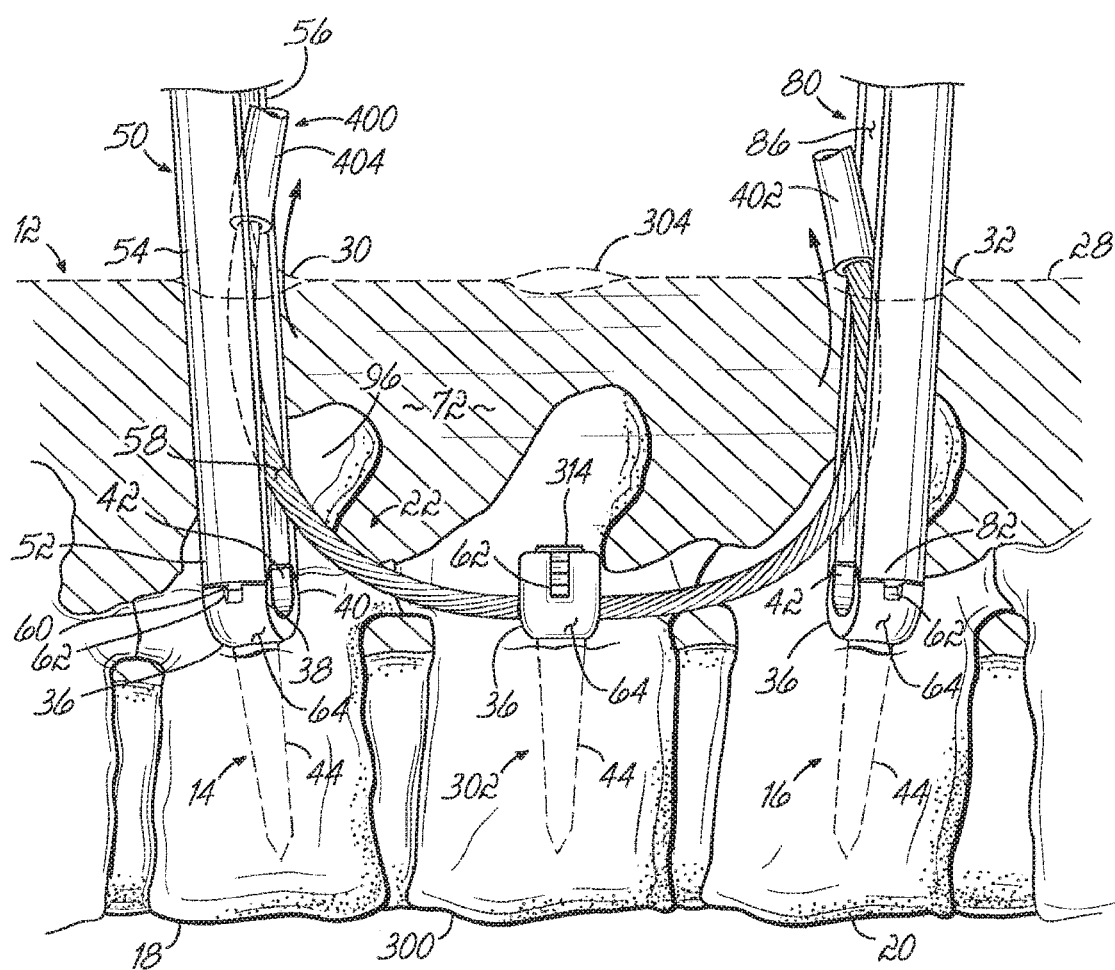
Figure 8A:
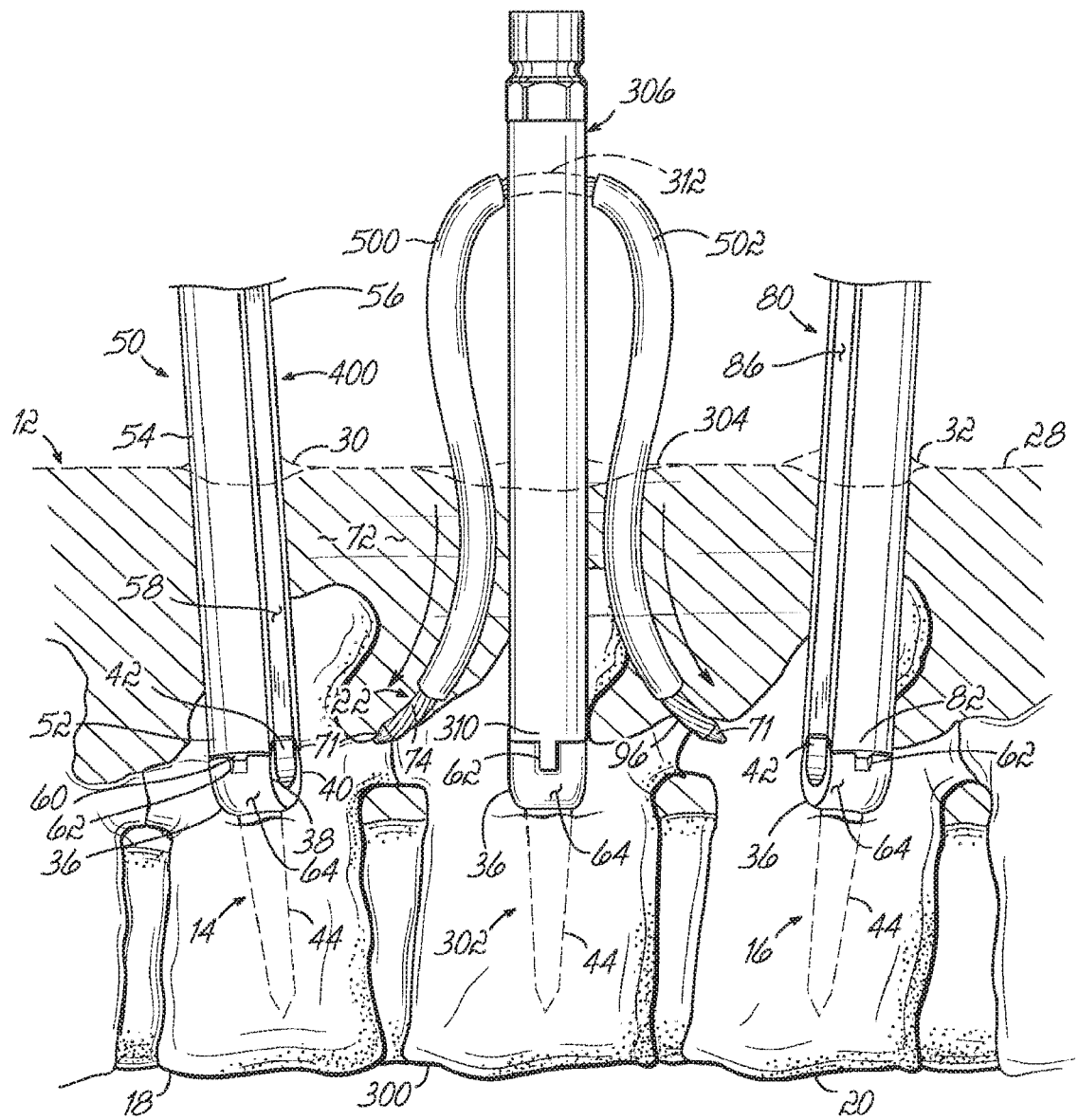
FIGS. 8A-8D are schematic views sequentially illustrating yet another method of inserting a flexible spinal stabilization system into a patient.
Figure 8B:
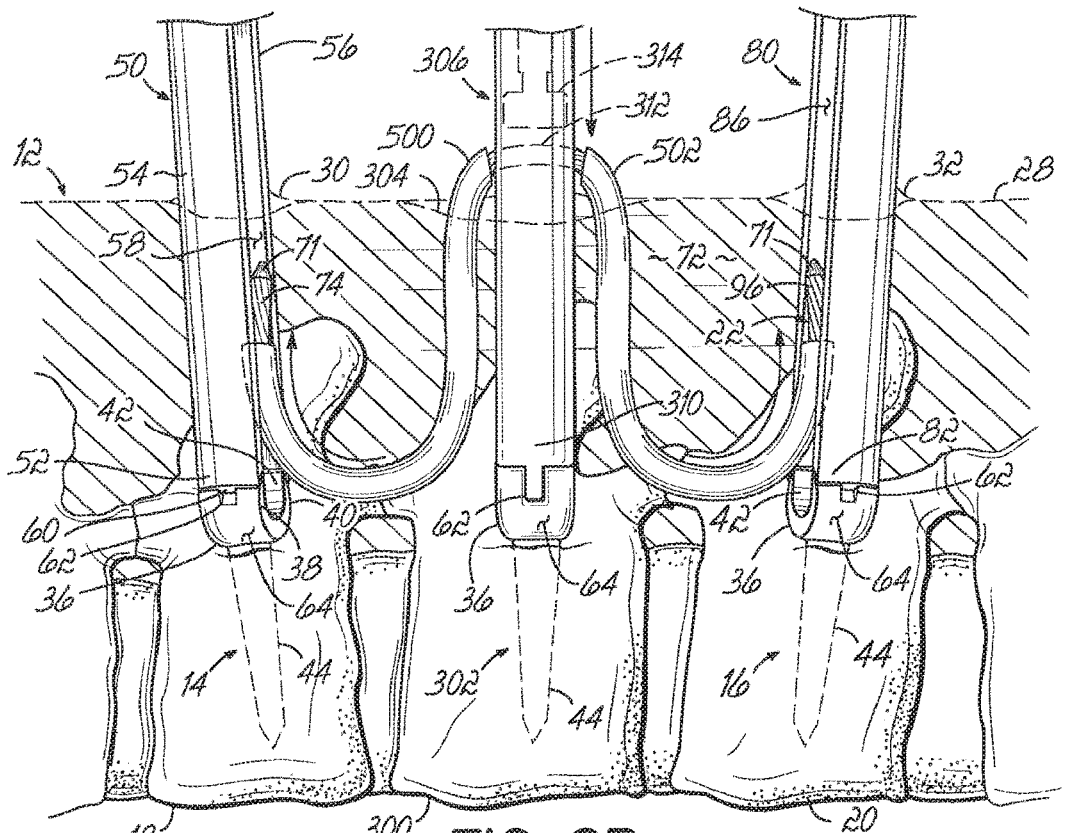
Figure 8C:
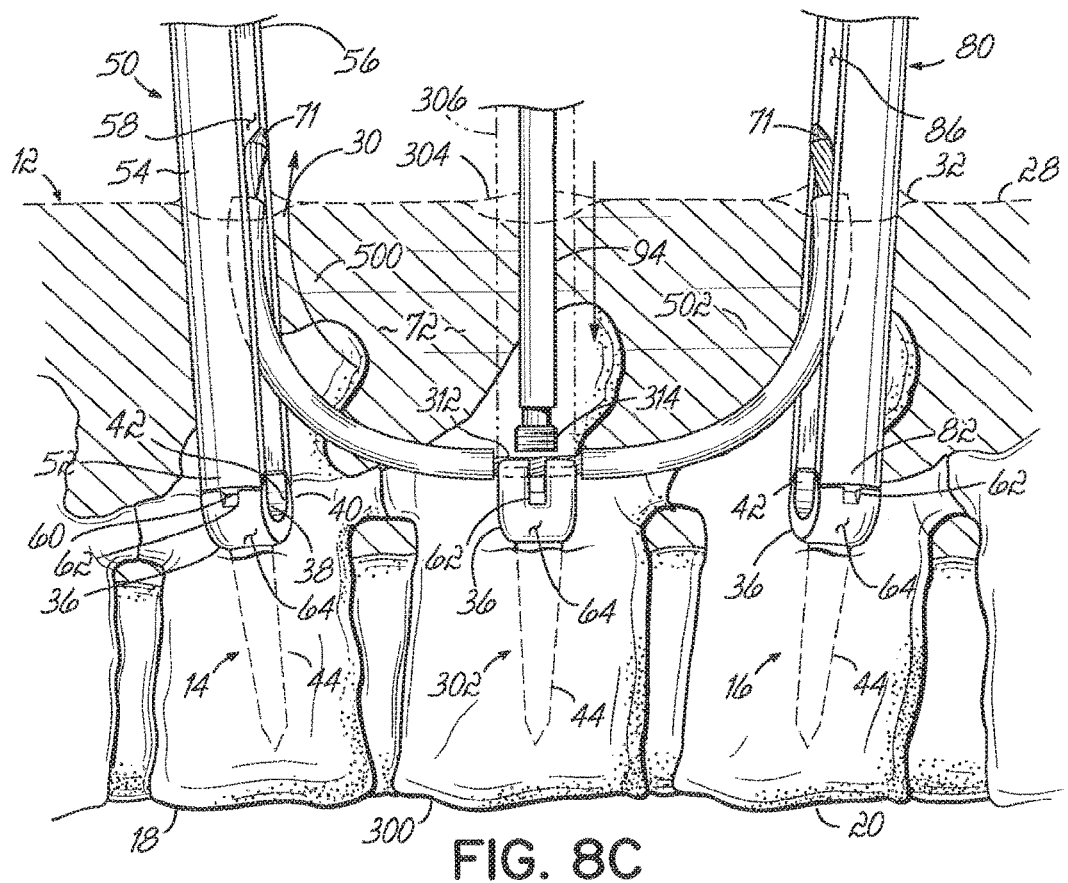
Figure 8D:
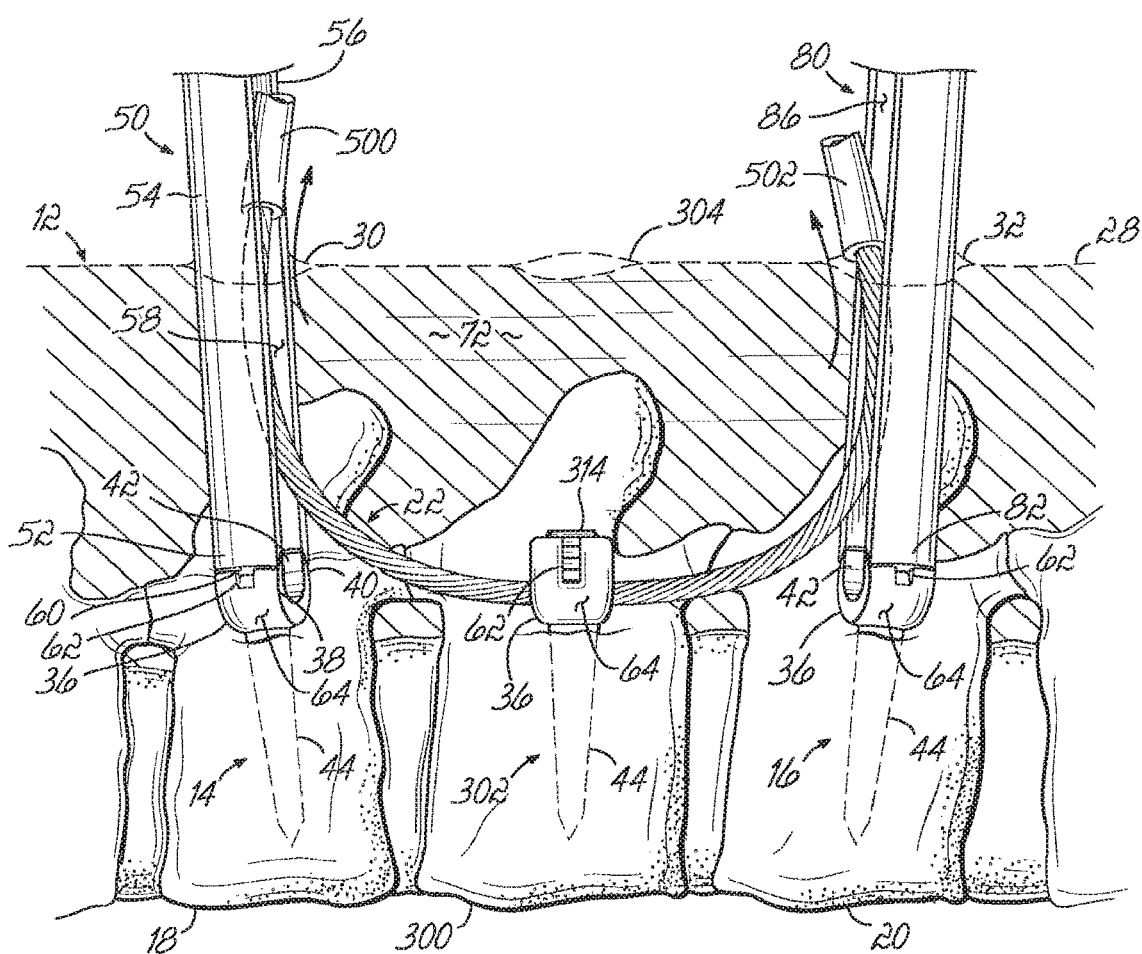

FIGS. 7A-7C illustrate another method of installing the stabilization system 10 for the purpose of multi-level treatment. Because the method uses many of the same components as the method shown in FIGS. 6A-6C, like reference numbers are used to refer to like structure. Additionally, only the differences between the methods are described below.

In this embodiment, a delivery device 400 is positioned over the connecting element 22. The delivery device 400 comprises a first sheath member 402 and a second sheath member 404, which may or may not have substantially the same shape and/or length. The delivery device 400 and connecting element 22 are inserted through the first incision 30 and along at least a portion of the first positioning tool 50 before the third end 310 of the third positioning tool 306 is coupled to the head 36 of the third vertebral anchor 302. Although FIG. 7A shows the first sheath member 402 spaced apart from the second sheath member 404 such that the third portion 312 of the connecting element 22 is exposed within the patient's body 12, the second sheath member 404 may alternatively be advanced over the third portion 312 during this insertion so as to abut the first sheath member 402.

Eventually the first sheath member 402 is directed past the third vertebral anchor 302 so that the third portion 312 of the connecting element 22 is positioned proximate the head 36 of the third vertebral anchor 302. If the second sheath member 404 abuts the first sheath member 402, the second sheath member 404 is retracted to expose the third portion 312. The third positioning tool 306 may then be directed downwardly to the third vertebral anchor 302 so that the third portion 312 is received in the elongated slot or cavity of the third positioning tool 306. After coupling the third end 310 of the third positioning tool 306 to the head 36 of the third vertebral anchor 302, the third portion 312 may be secured to the third vertebral anchor 302 using the fastener 314 or any other suitable technique.

Advantageously, the first sheath member 402 has a preformed curvature so that it curves slightly upwardly toward the patient's skin 28 after being advanced past the third vertebral anchor 302. The first sheath member 402 may eventually contact the second positioning tool 80, which may be used to facilitate directing the first sheath member 402 to the second incision 32. For example, the first sheath member 402 may be at least partially received in the elongated slot 86 and may slide along the elongated slot 86 when further advanced past the third vertebral anchor 302.

After the third portion 312 of the connecting element 22 is secured to the third vertebral anchor 302, the first and second sheath members 402, 404 may be removed from the patient's body 12 and connecting element 22. More specifically, the first sheath member 402 may be removed through the second incision 32 and from the connecting element 22 so as the leave the first portion 74 positioned in or proximate the elongated slot 86. The second sheath member 404 may be removed back through the first incision 30 and off the connecting element 22 so as to leave the second portion 96 positioned in or proximate the elongated slot 58. At this point, the first portion 74 may be secured to the second vertebral anchor 16 and the second portion 96 may be secured to the first vertebral anchor 14 using any of the techniques discussed above. It will be appreciated that the third positioning tool 306 may be removed through the third incision 304 before or after removing the first and second sheath members 402, 404 and/or securing the first and second portions 74, 96.

FIGS. 8A-8D illustrate yet another method of installing the stabilization system 10 for the purpose of multi-level treatment. Like reference numbers are once again used to refer to like structure from the other embodiments discussed above.

In this embodiment, the first, second, and third positioning tools 50, 80, 306 are inserted through the respective first, second, and third incisions 30, 32, 304 and coupled to the respective first, second, and third vertebral anchors 14, 16, 302. The connecting element 22 is inserted through the elongated slot in the third positioning tool 306 so that the first portion 74 extends generally toward the first positioning tool 50 and the second portion 96 extends generally toward the second positioning tool 80. A first delivery device 500 may then be positioned over the first portion 74 and a second delivery device 502 may be positioned over the second portion 96. The first and second delivery devices 500, 502 may be used to direct the first and second portions 74, 96 through the patient's body 12.

For example, the first delivery device 500 and the first portion 74 of the connecting element 22 may be inserted through the third incision 304 and along at least a portion of the third positioning tool 306. The third positioning tool 306 may be used for guidance and/or leverage to help direct the first delivery device 500 and first portion 74 along a path through the patient's body 12 and generally toward the first vertebral anchor 14. To this end, the third positioning tool 306 and its elongated slot may be used in a way similar to which the first positioning tool 50 and elongated slot 58 are used in the other embodiments discussed above. When the first delivery device 500 contacts the first vertebral anchor 14 and/or first positioning tool 50, it may be directed upwardly toward the first incision 30. For example, the first delivery device 500 may slide along the elongated slot 58 and exit the patient's body 12 through the first incision 30 when sufficiently advanced through the third incision 304. The tissue 72 within the patient's body 12 helps maintain the first delivery device 500 and connecting element 22 within the patient's body 12 between the first and third incisions 30, 304.

The second delivery device 502 and second portion 96 of the connecting element 22 may be inserted into the patient's body 12 in a similar manner. Specifically, the second delivery device 502 and second portion 96 may be inserted through the third incision 304 and generally toward the second vertebral anchor 16, using the third positioning tool 306 for guidance and/or leverage when needed. When the second delivery device 502 contacts the second vertebral anchor 16 and/or second positioning tool 80, it may be directed upwardly toward the second incision 32. For example, the second delivery device 502 may slide along the elongated slot 86 toward the second incision 32.

Next, the third portion 312 of the connecting element 22 may be pushed downwardly through the third positioning tool 306 and into the receiving channel 42 (FIG. 2) in the head 36 of the third vertebral anchor 302. Any suitable tool may be used to push the third portion 312, including the fastener 314 and driving tool 94 ultimately used to retain the third portion 312 within the receiving channel 42. As the third portion 312 is pushed downwardly, the first and second delivery devices 500, 502 are further advanced into the patient's body 12 as well. Thus, the first delivery device 500 eventually extends from the third vertebral anchor 302 to the first incision 30 and the second delivery device 502 eventually extends from the third vertebral anchor 302 to the second incision 32. After securing the third portion 312 to the third vertebral anchor 302 using the fastener 314 or any other suitable technique, the first and second delivery devices 500, 502 may be removed from the patient's body 12 through the respective first and second incisions 30, 32. Removing the first and second delivery devices 500, 502 exposes the first and second portions 74, 96, which may be secured to the respective first and second vertebral anchors 14, 16 using any of the techniques discussed above.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. For example, although the positioning tools are described above as being inserted through the same incisions used to inserted the vertebral anchors, the positioning tools may alternatively be inserted through separate incisions. Moreover, in an open surgical procedure there may be one or more large incisions through which two or more of the positioning tools are inserted. The invention in its broader aspects is therefore not limited to the specific details, representative apparatus and methods and illustrative examples shown and described. Accordingly, departures may be made from such details without departing from the scope or spirit of the inventor's general inventive concept.

What is claimed:

1. A system for anchoring a flexible connector between vertebra, the system comprising:
a flexible connector routable through a first receiving channel disposed in a first vertebral anchor head, the flexible connector securable in the first receiving channel using a first fastener;
a tensioning tool engageable with both a second vertebral anchor head and a portion of the flexible connector that is proximate the second vertebral anchor head to direct the flexible connector into a second receiving channel disposed in the second vertebral anchor head via a bottom tensioner portion that is insertable through an elongated slot disposed in a distal portion of the tensioning tool that is in communication with the second receiving channel, the tensioning tool further comprising a gripping element positioned at a proximal end thereof, the gripping element disposed on a proximal end of the tensioning tool and including a first arm pivotable relative to a second arm fixed to the proximal end of the tensioning tool, the first arm including a first member for securing an additional portion of the flexible connector extendable upward through the proximal end of the tensioning tool, the first arm pivotable relative to the second arm to pull the additional portion of the flexible connector proximally to apply tension to the flexible connector.

2. The system of claim 1, wherein the tensioning tool further comprises a conduit disposed therein extending from the proximal end towards a distal end thereof, wherein the conduit facilitates delivery of a second fastener for securing the flexible connector in the second receiving channel disposed in the second vertebral anchor head.

3. The system of claim 1, wherein the elongated slot disposed in the tensioning tool extends from a distal end towards the proximal end of the tensioning tool.

4. The system of claim 3, wherein the elongated slot disposed in the tensioning tool extends from the distal end to the proximal end of the tensioning tool.

5. The system of claim 1, wherein the first receiving channel has internal threads and the first fastener has external threads engageable with the internal threads of the first receiving channel and wherein advancement of the first fastener into the first receiving channel secures the flexible connector therein.

6. The system of claim 5, wherein the second receiving channel has internal threads and the system further comprises a second fastener that has external threads engageable with the internal threads of the second receiving channel and wherein advancement of the second fastener into the second receiving channel secures the flexible connector therein.

7. The system of claim 1, wherein the bottom tensioner portion comprises a positioning member engageable with the flexible connector to route the flexible connector through the second receiving channel.

8. The system of claim 7, wherein the positioning member is further engageable with the second vertebral anchor head to stabilize the second vertebral anchor head during tensioning.

9. The system of claim 1, further comprising a flexible delivery device positionable over a proximal portion of the flexible connector for advancing the flexible connector to and through the second receiving channel towards the first receiving channel.

10. The system of claim 9, wherein the flexible delivery device comprises polyethylene tubing comprising a rigidity greater than a rigidity of the flexible connector.

11. The system of claim 9, wherein the flexible delivery device comprises a tubular element.

12. The system of claim 1, wherein the flexible connector comprises a leading end portion comprising a rigidity greater than a rigidity of the remainder of the flexible connector.

13. The system of claim 12, wherein the leading end portion comprises a separate component mounted to the flexible connector.

14. The system of claim 12, wherein the leading end portion comprises a tapered tip to facilitate movement through tissue.

15. A device, comprising:
a tensioning tool engageable with both a second vertebral anchor head and a portion of a flexible connector that is proximate the second vertebral anchor head to direct the flexible connector into a second receiving channel disposed in the second vertebral anchor head via a bottom tensioner portion that is insertable through an elongated slot disposed in a distal portion of the tensioning tool that is in communication with the second receiving channel, the tensioning tool further comprising a gripping element positioned at a proximal end thereof, the gripping element including a first arm pivotable relative to a second arm fixed to the proximal end of the tensioning tool, the first arm including a first member for securing an additional portion of the flexible connector extendable upward through the proximal end of the tensioning tool, the first arm pivotable relative to the second arm to pull the additional portion of the flexible connector proximally to apply tension to the flexible connector when the flexible connector is secured in a first receiving channel disposed in a first vertebral anchor head using a first fastener.

16. The system of claim 15, wherein the tensioning tool further comprises a conduit disposed therein extending from the proximal end towards a distal end thereof, wherein the conduit facilitates delivery of a second fastener for securing the flexible connector in the second receiving channel disposed in the second vertebral anchor head.

17. The system of claim 15, wherein the elongated slot disposed in the tensioning tool extends from a distal end towards the proximal end of the tensioning tool.

18. The system of claim 15, wherein the bottom tensioner portion comprises a positioning member engageable with the flexible connector to route the flexible connector through the second receiving channel.

19. The system of claim 18, wherein the positioning member is further engageable with the second vertebral anchor head to stabilize the second vertebral anchor head during tensioning.

* * * * *